United States Patent
Omarsson et al.

(10) Patent No.: US 11,337,840 B2
(45) Date of Patent: May 24, 2022

(54) ORTHOPEDIC DEVICE

(71) Applicant: Ossur Iceland ehf, Reykjavik (IS)

(72) Inventors: Bjorn Omarsson, Reykjavik (IS);
Christophe Valois, Reykjavik (IS);
Arni Thor Ingimundarson, Reykjavik (IS); Sindri Pall Sigurdsson, Reykjavik (IS); Cyril Chuzel, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 0 days.

(21) Appl. No.: 16/244,374

(22) Filed: Jan. 10, 2019

(65) Prior Publication Data

US 2019/0142620 A1    May 16, 2019

Related U.S. Application Data

(63) Continuation of application No. 15/822,806, filed on Nov. 27, 2017, now Pat. No. 10,966,851, which is a
(Continued)

(51) Int. Cl.
*A61F 5/01* (2006.01)
*A61F 13/06* (2006.01)
(Continued)

(52) U.S. Cl.
CPC .......... *A61F 5/0109* (2013.01); *A61F 5/0123* (2013.01); *A61F 5/0125* (2013.01);
(Continued)

(58) Field of Classification Search
CPC .... A61F 5/0109; A61F 5/0123; A61F 5/0125; A61F 5/0193; A61F 5/32; A61F 5/34;
(Continued)

(56) References Cited

U.S. PATENT DOCUMENTS

| | | |
|---|---|---|
| 1,529,928 A | 3/1925 | Schuster |
| 1,965,314 A | 7/1934 | Henderson |

(Continued)

FOREIGN PATENT DOCUMENTS

| | | |
|---|---|---|
| CN | 1354643 A | 6/2002 |
| CN | 2604894 A1 | 3/2004 |

(Continued)

OTHER PUBLICATIONS

Product Information, "BORT AsymmetricPlus, No. 114900, Unit PCE", downloaded Mar. 31, 2014, 3 pages. Retrieved at http://shop.bort.de/en/produkt-details.aspx?ProductNo=114900.
(Continued)

*Primary Examiner* — Camtu T Nguyen
(74) *Attorney, Agent, or Firm* — Workman Nydegger

(57) ABSTRACT

An orthopedic device comprises a main body defining an outer surface and a cuff extending from an end portion of the main body with frictional material disposed on an inner surface of the first cuff. A hinge is connected to the main body and terminates along the main body short of the cuff. The cuff is arranged to fold over the outer surface of the main body in a disengaged configuration, such that the outer surface of the first cuff is adjacently against the outer surface of the main body.

11 Claims, 17 Drawing Sheets

Related U.S. Application Data continuation-in-part of application No. 15/672,593, filed on Aug. 9, 2017, now Pat. No. 10,758,393.

(60) Provisional application No. 62/372,367, filed on Aug. 9, 2016.

(51) Int. Cl.
*A61F 5/34* (2006.01)
*D04B 1/18* (2006.01)
*D04B 1/26* (2006.01)
*D04B 1/10* (2006.01)
*A61F 5/32* (2006.01)
*D04B 21/14* (2006.01)

(52) U.S. Cl.
CPC .............. *A61F 5/34* (2013.01); *A61F 13/061* (2013.01); *D04B 1/104* (2013.01); *D04B 1/18* (2013.01); *D04B 1/265* (2013.01); *A61F 5/0193* (2013.01); *A61F 5/32* (2013.01); *A61F 2005/0165* (2013.01); *A61F 2005/0176* (2013.01); *D04B 21/14* (2013.01); *D10B 2403/032* (2013.01); *D10B 2501/061* (2013.01); *D10B 2509/028* (2013.01)

(58) Field of Classification Search
CPC ............ A61F 2005/0165; A61F 5/0176; A61F 13/061; D04B 1/104; D04B 1/18; D04B 1/265; D04B 21/14; D10B 2403/032; D10B 2501/061; D10B 2509/028
See application file for complete search history.

(56) References Cited

U.S. PATENT DOCUMENTS

| | | | |
|---|---|---|---|
| 2,186,572 A | 1/1940 | Boepple | |
| 3,059,834 A | 10/1962 | Hausammann | |
| 3,255,613 A * | 6/1966 | Burd | A41B 11/12 66/172 R |
| 3,306,081 A | 2/1967 | Miles et al. | |
| 3,478,748 A | 11/1969 | Bjorn-Larsen | |
| 3,496,944 A | 2/1970 | Cuozzi | |
| 3,638,658 A | 2/1972 | Becker et al. | |
| 3,975,929 A | 8/1976 | Fregeolle | |
| 4,176,665 A | 12/1979 | Terpening | |
| 4,201,203 A | 5/1980 | Applegate | |
| 4,379,463 A | 4/1983 | Meier et al. | |
| 4,466,428 A | 8/1984 | McCoy | |
| 4,492,227 A | 1/1985 | Senn et al. | |
| 4,870,956 A | 10/1989 | Fatool et al. | |
| 4,908,037 A | 3/1990 | Ross | |
| 5,036,837 A | 8/1991 | Mitchell et al. | |
| 5,139,477 A | 8/1992 | Peters | |
| 5,277,697 A | 1/1994 | France et al. | |
| 5,334,135 A | 8/1994 | Grim et al. | |
| 5,385,538 A | 1/1995 | Mann | |
| 5,497,513 A * | 3/1996 | Arabeyre | A61F 13/08 2/16 |
| 5,520,622 A | 5/1996 | Bastyr et al. | |
| 5,538,488 A | 7/1996 | Villepigue | |
| 5,695,452 A | 12/1997 | Grim et al. | |
| 5,711,029 A | 1/1998 | Visco et al. | |
| 5,728,057 A | 3/1998 | Ouellette et al. | |
| 5,728,058 A | 3/1998 | Ouellette et al. | |
| 5,730,710 A | 3/1998 | Eichhorn et al. | |
| 5,769,809 A | 6/1998 | Witzel | |
| 5,865,776 A | 2/1999 | Springs | |
| D422,709 S | 4/2000 | Caswell | |
| 6,059,834 A | 5/2000 | Springs | |
| 6,149,616 A | 11/2000 | Szlema et al. | |
| D435,145 S | 12/2000 | Lindsey | |
| 6,344,104 B1 * | 2/2002 | Sekiya | B29C 37/0067 156/231 |
| 6,371,933 B1 | 4/2002 | Gardon-Mollard | |
| D457,293 S | 5/2002 | Maurer | |
| 6,408,445 B1 | 6/2002 | Matthews | |
| 6,412,311 B1 | 7/2002 | Nakai | |
| 6,430,970 B1 | 8/2002 | Gardon-Mollard et al. | |
| 6,440,526 B1 | 8/2002 | Gamble et al. | |
| 6,523,729 B1 | 2/2003 | Gardon-Mollard | |
| 6,592,539 B1 | 7/2003 | Einarsson et al. | |
| 6,634,190 B2 | 10/2003 | Didier-Laurent | |
| D492,787 S | 7/2004 | Weaver, II et al. | |
| 6,838,402 B2 | 1/2005 | Harris et al. | |
| 7,017,376 B2 | 3/2006 | Meckley et al. | |
| 7,025,738 B2 | 4/2006 | Hall | |
| 7,076,973 B1 | 7/2006 | Chesebro, Jr. et al. | |
| 7,083,586 B2 | 8/2006 | Simmons et al. | |
| 7,198,610 B2 | 4/2007 | Ingimundarson et al. | |
| 7,273,464 B2 | 9/2007 | Reinhardt | |
| D555,339 S | 11/2007 | Chang | |
| D572,827 S | 7/2008 | Reinhardt et al. | |
| D574,084 S | 7/2008 | Reinhardt | |
| 7,473,236 B1 | 1/2009 | Mathewson | |
| 7,517,331 B2 | 4/2009 | Reinhardt et al. | |
| D601,705 S | 10/2009 | Bauerfeind et al. | |
| 7,625,350 B2 | 12/2009 | Hunter et al. | |
| 7,699,195 B2 | 4/2010 | Scott | |
| 7,749,181 B2 | 7/2010 | Simmons et al. | |
| D626,241 S | 10/2010 | Sagnip et al. | |
| 7,819,830 B2 | 10/2010 | Sindel et al. | |
| D629,115 S | 12/2010 | Robertson | |
| D630,333 S | 1/2011 | Chiang | |
| 7,871,388 B2 | 1/2011 | Brown | |
| D635,266 S | 3/2011 | Chiang | |
| D635,267 S | 3/2011 | Chiang | |
| 7,896,827 B2 | 3/2011 | Ingimundarson et al. | |
| 7,943,219 B2 | 5/2011 | Krueger | |
| 7,959,590 B2 | 6/2011 | Scott | |
| 8,025,632 B2 | 9/2011 | Einarsson | |
| 8,043,242 B2 | 10/2011 | McSpadden et al. | |
| 8,048,014 B2 | 11/2011 | Brown | |
| 8,066,654 B2 | 11/2011 | Sandifer et al. | |
| D654,182 S | 2/2012 | Chiang | |
| 8,118,765 B2 | 2/2012 | Magnusson | |
| D657,063 S | 4/2012 | Chiang | |
| D665,950 S | 8/2012 | Rokitta | |
| 8,328,747 B2 | 12/2012 | Matsunaga | |
| D683,118 S | 5/2013 | Pauk | |
| 8,435,197 B2 | 5/2013 | Vollbrecht et al. | |
| 8,911,389 B2 | 12/2014 | Reinhardt et al. | |
| 8,950,013 B2 | 2/2015 | Bates | |
| 9,017,274 B2 | 4/2015 | Forbes et al. | |
| 9,066,546 B2 | 6/2015 | Getzwiller | |
| 9,113,998 B2 | 8/2015 | Romo | |
| D741,622 S | 10/2015 | Jensen et al. | |
| 9,173,763 B2 | 11/2015 | Gilmer et al. | |
| D759,826 S | 6/2016 | Martinez et al. | |
| 9,393,147 B2 | 7/2016 | Scheuermann et al. | |
| D777,468 S | 1/2017 | Currier | |
| 9,545,328 B2 | 1/2017 | Hess et al. | |
| D778,563 S | 2/2017 | Kanata | |
| D783,207 S | 4/2017 | Lindsey | |
| D783,970 S | 4/2017 | Kanata | |
| D788,540 S | 6/2017 | Mock | |
| D789,547 S | 6/2017 | Matfus et al. | |
| D794,932 S | 8/2017 | Parrett et al. | |
| 9,744,063 B2 | 8/2017 | Huffa et al. | |
| D796,809 S | 9/2017 | Williams, Jr. | |
| 9,750,643 B2 | 9/2017 | Convert et al. | |
| D804,043 S | 11/2017 | Gildersleeve | |
| D812,236 S | 3/2018 | Burke et al. | |
| D816,234 S | 4/2018 | Calvello et al. | |
| D831,221 S | 10/2018 | Smith | |
| 10,159,592 B2 | 12/2018 | Ingimundarson et al. | |
| 10,165,803 B2 | 1/2019 | Hoeven | |
| 10,195,067 B2 | 2/2019 | Grange et al. | |
| D843,684 S | 3/2019 | Hamilton et al. | |
| 10,231,860 B2 | 3/2019 | Forbes et al. | |
| 2003/0065357 A1 * | 4/2003 | Dedo | A61B 17/1322 606/203 |
| 2003/0114782 A1 | 6/2003 | Chiang et al. | |

(56) References Cited

U.S. PATENT DOCUMENTS

| | | |
|---|---|---|
| 2003/0216676 A1 | 11/2003 | Gardon-Mollard |
| 2004/0153017 A1 | 8/2004 | Simmons et al. |
| 2005/0020951 A1 | 1/2005 | Gaylord et al. |
| 2006/0151550 A1 | 7/2006 | Chevalier |
| 2006/0246802 A1 | 11/2006 | Hughes et al. |
| 2007/0060853 A1 | 3/2007 | Sindel et al. |
| 2007/0197944 A1 | 8/2007 | Bruce et al. |
| 2008/0139982 A1 | 6/2008 | Magnusson |
| 2009/0156973 A1 | 6/2009 | Scott |
| 2010/0036303 A1 | 2/2010 | Bauerfeind et al. |
| 2010/0152635 A1 | 6/2010 | Borden |
| 2011/0137220 A1 | 6/2011 | Vollbrecht et al. |
| 2011/0137223 A1* | 6/2011 | Daniel ............... A61L 15/12 602/76 |
| 2011/0172582 A1 | 7/2011 | Darian |
| 2011/0282254 A1* | 11/2011 | Gadlage ............ A61F 5/0118 602/3 |
| 2012/0141750 A1 | 6/2012 | Taylor |
| 2012/0165713 A1 | 6/2012 | Forbes et al. |
| 2012/0165714 A1 | 6/2012 | Forbes et al. |
| 2012/0232448 A1 | 9/2012 | Wüst |
| 2012/0277649 A1 | 11/2012 | Matsuo et al. |
| 2013/0022794 A1 | 1/2013 | Ng et al. |
| 2013/0053743 A1 | 2/2013 | Reinhardt et al. |
| 2013/0053744 A1 | 2/2013 | Convert et al. |
| 2013/0110023 A1 | 5/2013 | Scheuermann et al. |
| 2013/0116609 A1 | 5/2013 | Matsuo et al. |
| 2013/0211304 A1 | 8/2013 | Romo et al. |
| 2013/0251962 A1 | 9/2013 | Reid, Jr. |
| 2013/0312294 A1 | 11/2013 | Tang |
| 2013/0333706 A1 | 12/2013 | Bauerfeind |
| 2014/0079900 A1 | 3/2014 | Ramirez |
| 2014/0303534 A1 | 10/2014 | Huffa et al. |
| 2015/0032041 A1 | 1/2015 | Ingimundarson et al. |
| 2015/0038891 A1 | 2/2015 | Lipton et al. |
| 2015/0121657 A1 | 5/2015 | Ingimundarson et al. |
| 2015/0272767 A1 | 10/2015 | Field |
| 2015/0290014 A1 | 10/2015 | Anglada et al. |
| 2016/0081835 A1 | 3/2016 | Grange et al. |
| 2016/0324675 A1 | 11/2016 | Gomez et al. |
| 2017/0000199 A1* | 1/2017 | Guzman ............ A41D 13/087 |
| 2017/0020707 A1 | 1/2017 | Duport et al. |
| 2017/0027719 A1 | 2/2017 | Bache et al. |
| 2017/0119568 A1 | 5/2017 | Chiang et al. |
| 2018/0042754 A1 | 2/2018 | Ingimundarson et al. |
| 2019/0037937 A1 | 2/2019 | Ito et al. |
| 2019/0175377 A1 | 6/2019 | Forbes et al. |

FOREIGN PATENT DOCUMENTS

| | | |
|---|---|---|
| CN | 102085126 A | 6/2011 |
| CN | 102665617 A | 9/2012 |
| CN | 103458834 A | 12/2013 |
| CN | 105228566 A | 1/2016 |
| CN | 105939694 A | 9/2016 |
| DE | 102010019405 A1 | 8/2011 |
| EP | 2283795 A1 | 2/2011 |
| EP | 2536370 B1 | 1/2015 |
| FR | 2775431 A1 | 9/1999 |
| FR | 2807644 A1 | 10/2001 |
| FR | 2879405 A1 | 6/2006 |
| WO | 9105498 A1 | 5/1991 |
| WO | 9944548 A1 | 9/1999 |
| WO | 03096851 A2 | 11/2003 |
| WO | 2008006142 A1 | 1/2008 |
| WO | 2012003992 A1 | 1/2012 |
| WO | 2017135473 A1 | 8/2017 |
| WO | 2018031618 A1 | 2/2018 |

OTHER PUBLICATIONS

Product Information, "BORT AsymmetricPlus, No. 114700, Unit PCE", downloaded Mar. 31, 2014, 3 pages. Retrieved at http://shop.bort.de/en/produkt-details.aspx?ProductNo=114700.
Brochure, "BORT Asymmetric Plus, Die Mehrwert-Orthese bei Patella-Luxation", downloaded Aug. 2012. 16 pages. Retrieved at http://www.bort.com.
Catalog, "Bracing and Supports Catalog," Ottobock, 2015, pp. 1-100.
Catalog, "Continuum of Care for Orthopedic Clinics," BSNmedical, 2016, pp. 1-48.
Catalog, "Product Guide," Mueller Sports Medicine, 2016, pp. 1-92.
Catalog, "Aircast Procare Exos Product Catalog," DJO Global, 2014, pp. 1-144.
Brochure, "Action Reliever Active Pain Relief for Knee Osteoarthritis," Thuasne, 2017, 2 Pages.
Catalog, "Catalogue 2017," Bort Medical, 2017, pp. 1-196.
Catalog, "2017 International Product Catalog," BREG, 2017, pp. 1-100.
Catalog, "International Catalogue," Gibaud, Jun. 2014, pp. 1-92.
Product Information, "GenuForce," DJO Global, retrieved from www.djoglobal.com/products/donjoy/genuforce, downloaded Nov. 9, 2017, 3 Pages.
Product Information, "Genumedi & Genumedi Extra Wide," Medi, retrieved from https://mediusa.com/portfolio-item/genumedi/, downloaded Nov. 9, 2017, 5 Pages.
Product Information, "Genumedi pro," Medi, retrieved from http://mediusa.com/portfolio-item/genumedi-pro/, downloaded Nov. 9, 2017, 5 Pages.
Product Information, "Genumedi PT," Medi, retrieved from http://mediusa.com/portfolio-item/genumedi-pt/, downloaded Nov. 9, 2017, 5 Pages.
Product Information, "GenuTrain P3," Bauerfeind, downloaded Nov. 9, 2017, 3 Pages.
Product Information, "Lumbamed Basic," Medi, retrieved from http://mediusa.com/portfolio-item/lumbamed-basic/, downloaded Nov. 9, 2017, 5 Pages.
Product Information, "Lumbamed Plus," Medi, retrieved from http://mediusa.com/portfolio-item/lumbamed-plus/, downloaded Nov. 9, 2017, 7 Pages.
Product Information, "LumboTrain," Bauerfeind, downloaded Nov. 9, 2017, 3 Pages.
Product Information, "LumboTrain Lady," Bauerfeind, downloaded Nov. 9, 2017, 3 Pages.
Product Information, "MalleoTrain," Bauerfeind, downloaded Nov. 9, 2017, 3 Pages.
Catalog, "OA & Injury Solutions Catalogue," OSSUR, 2017, pp. 1-121.
Catalog, "Product Catalog Supports and Orthoses," Bauerfeind, 2015, pp. 1-72.
Catalog, "Push for Freedom," Push Braces, pp. 1-28.
Product Information, "Sports Ankle Support Dynamic," Bauerfeind, downloaded Nov. 9, 2017, 2 Pages.
Product Information, "Sports Back Support," Bauerfeind, downloaded Nov. 9, 2017, 3 Pages.
Product Information, "Sports Elbow Support," Bauerfeind, downloaded Nov. 9, 2017, 4 Pages.
Product Information, "Sports Knee Support," Bauerfeind, downloaded Nov. 9, 2017, 3 Pages.
Catalog, "Orthopedic Products 2016," Thuasne, 2016, pp. 1-32.
International Search Report from PCT Application No. PCT/US2017/046028, dated Nov. 7, 2017.
Office Action from corresponding Application No. 201780053924.X, dated Jul. 23, 2020.
International Search Report and Written Opinion from PCT Application No. PCT/US2018/062420, dated Mar. 14, 2019.
Chinese Office Action from corresponding CN Application No. 201880076188.4, dated May 10, 2021.

* cited by examiner

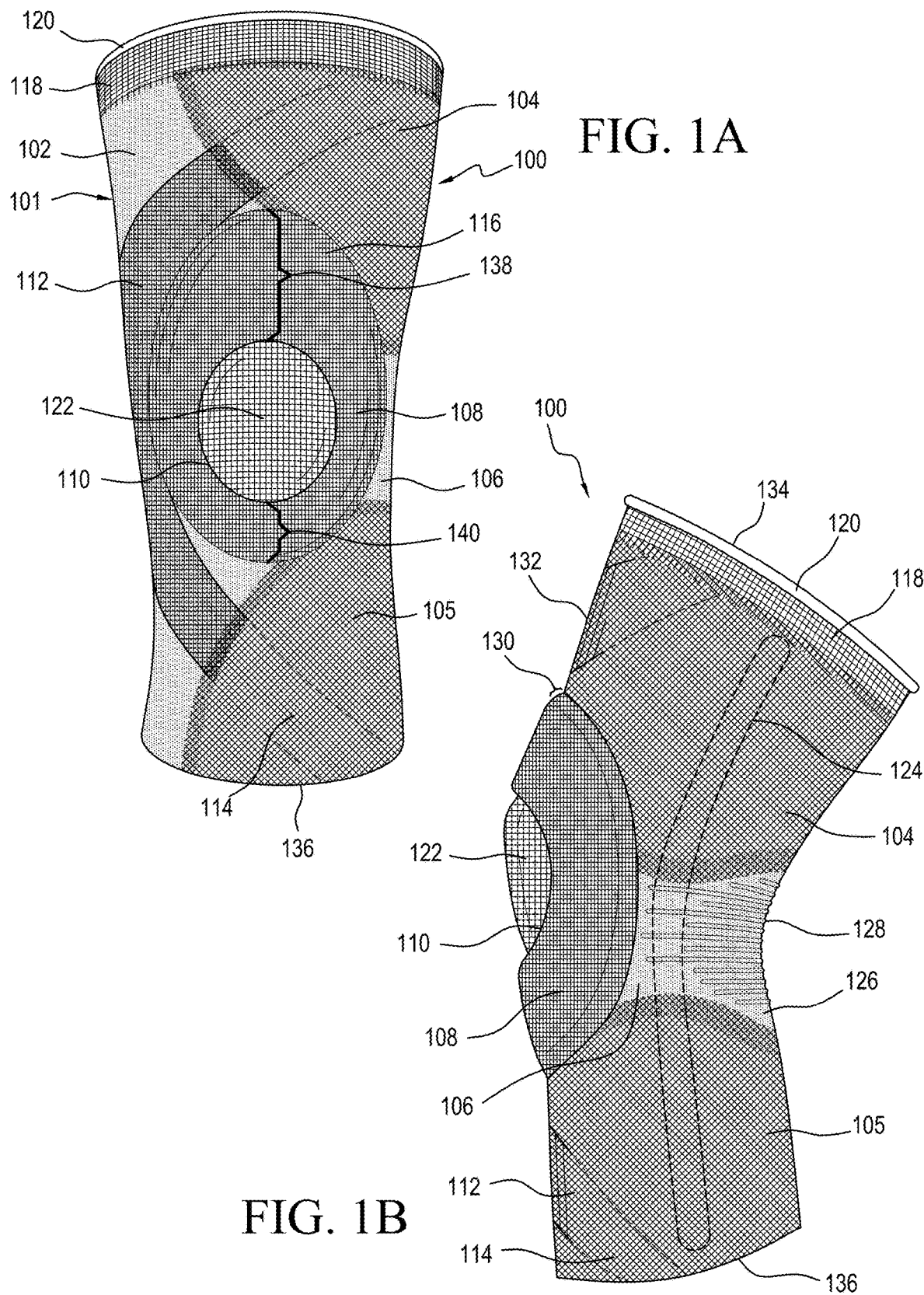

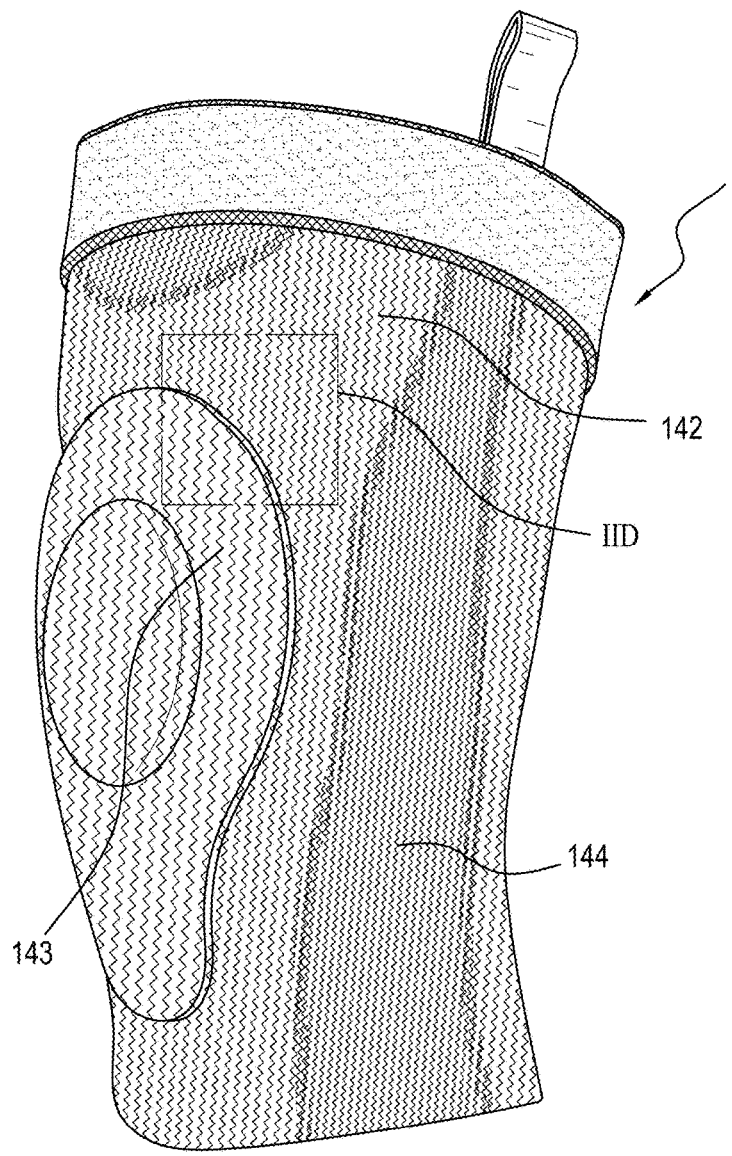
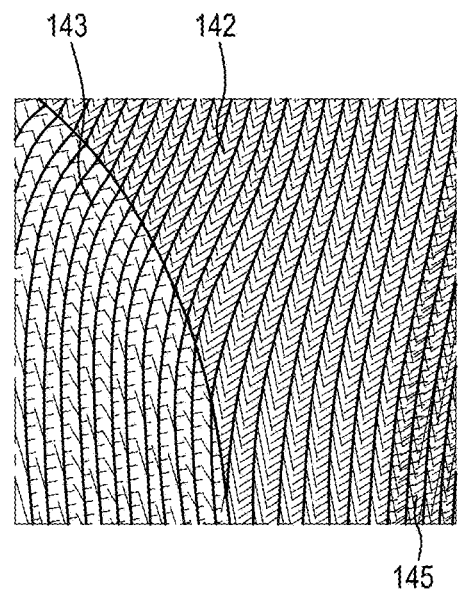
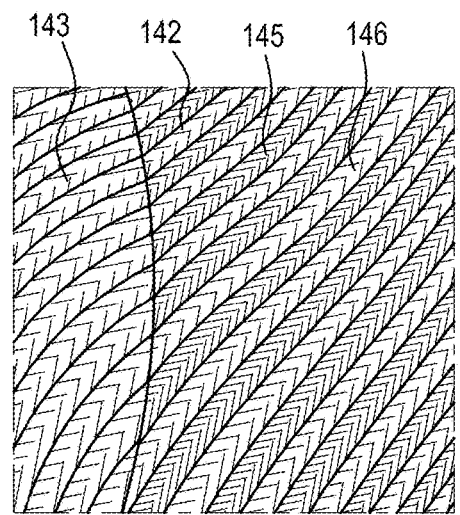
FIG. 2C
FIG. 2D
FIG. 2E

ORTHOPEDIC DEVICE

FIELD OF ART

The embodiments of this disclosure are directed to an orthopedic device arranged for intimately fitting to, immobilizing, restricting, supporting, and guiding anatomical segments or joints.

BACKGROUND

Orthopedic braces and supports are arranged to restrict, inhibit, immobilize, or otherwise control motion about anatomical segments or joints of the human body. These braces and supports provide compression, support, and stability. Many known braces and supports incorporate rigid members and hinges for immobilizing a joint or facilitating movement of the joint. Orthopedic bracing has tended toward greater rigidity to provide ultimate immobilization with a reduced margin of error in mobility, thus many device designs are over-engineered.

There tends to be an inverse relationship between the rigidity of the device and patient comfort/compliance. The more rigid the device is, the less likely it will be worn, especially over extended periods of time. If the patient removes a required device to increase comfort, rehabilitation may be hampered and risk of further injury may be elevated.

Flexible braces and supports exist which offer compression, support, and stability. However, many are formed from synthetic materials such as Neoprene. These types of braces can give rise to allergic reactions and get hot. Because they typically rely on a sheet of homogeneous material, they lack areas having different properties, and may be ill-fitting or ineffective as a joint requires different areas of compression.

Orthopedic devices, such as flexible orthopedic devices and sleeves, provide anatomical fit by conforming to a user's anatomy for physiologically correct support. They are flexible and arranged for contouring to a body or joint to minimize movement restriction and discomfort. The devices may be configured to stretch in different ways to enable greater muscle stability. In view of their sizing and fit, these devices not only provide support but also improve circulation, and reduce pain and inflammation. Other types of flexible orthopedic devices and/or sleeves may include neoprene and/or other textiles and materials, and may include other tubular configurations or other shapes and configurations as well.

Unfortunately, known orthopedic devices are often lacking in adequate strapping and instead rely on their elasticity for being maintained on a limb and/or preventing unwanted migration of the device. These devices are limited to uniform elasticity, whereas the user may require different degrees of elasticity depending on where the device is intended be placed over the anatomy, for different types of recoveries from different types of pathologies, and/or for being retained on the user and treatment of specific anatomy. Such devices may not provide sufficient support, and rather offer more proprioceptive than functional capabilities.

In view of the tubular nature of many orthopedic devices including flexible orthopedic devices or sleeves, an issue often arises in migration control. Taking for instance a knee support, as the leg is conical, it is difficult to control the migration of the knee support during repeated movement between flexion and extension. Often straps are used to hold the support on the leg, or light frictional material is applied on the interior of the support. The straps may exert too much compressive force on the leg, creating discomfort and impeding activities of the user.

The frictional material which serves to hold the orthopedic device in place must have low frictional qualities so as to allow the user to slide the support on the leg, which has the undesired effect of reducing effectiveness of anti-migration means. Compensating for the use of low friction materials with a more highly compressive body panel in order to better hold the device in place also creates problems, as highly compressive body panels are extremely difficult to don, and when donned are uncomfortable for a user and are thus not suitable for extended use. These current means for migration control require improvement to balance and optimize migration control, ease of use, and donning and doffing of the support.

Strap designs in existing devices mistake the proper placement of straps and thus do not offer optimal support for patients suffering from pathologies such as osteoarthritis. Many orthopedic devices feature straps that are connected to each other at a crossing or intersecting point on the orthopedic device, usually directly at and over the hinge located on a medial or lateral side of the device. However, this is not an ideal placement of the intersection of the straps, as it does not effectively unload the knee, and thus does not effectively treat the underlying condition, such as osteoarthritis. Straps may also be difficult to repeatedly apply and adjust. Straps may stray from their intended location on the brace, reducing their effectiveness. Straps may also get tangled with each other or be damaged by external forces.

Another issue that arises in orthopedic devices is difficulty in donning and doffing due to poor grip on the device by a user. Gripping the tubular body directly can lead to undesired stretching and damage to the device, while also being difficult for a user. Certain orthopedic devices allow for a tab that guides a strap on an outside surface of the device to serve additionally as a "pull tab," but this needs improvement as it can lead to damage of the tab that must also guide a strap, and may also be inconvenient due to its location, as the tab could catch on objects, further causing damage and inconvenience and making long term use difficult.

Orthopedic devices often comprise a patella support for maintaining the patella in position to prevent dislocation. However, patella supports are frequently ineffective at holding the patella in position as the patella supports themselves, which often take the form of a pad attachable within a tubular body, are prone to migration or translation along a user's skin. Patella supports also can create pressure points or be inflexible which further adds to user discomfort.

Flexible orthopedic devices often do not account for or properly address the compressive, supportive, restrictive, elastic, or breathability requirements of various distinct areas on a limb. As such, they may provide too much compression and too little breathability in some areas, while not providing enough compression in others. Such devices may fail to properly treat various pathologies or user-specific conditions.

From the foregoing, there is a need for an orthopedic device that provides improved migration control, comfort, and functionality, while being easier to don/doff, and providing enhanced biomechanical support of a joint, such as by properly locating straps and providing effective patella support, and properly arranging areas of required elasticity and/or restriction.

SUMMARY

An orthopedic device according to the disclosure arranged for intimately fitting the limb and joint of the user solves the problem of rigid braces and supports deterring a user from proper use and not facilitating joint motion activities. The orthopedic device also solves the problem of orthopedic devices, including flexible orthopedic devices and sleeves, having ineffective migration control and being difficult to don/doff. The orthopedic device solves the problem of straps intersecting at a location that is ineffective for treating pathologies such as osteoarthritis, particularly of the knee. The orthopedic device solves the problem of straps being cumbersome to use due to straying from intended locations, tangling, or being damaged by external forces. The orthopedic device solves the problem of patella supports being ineffective due to undesired translation along skin, being inflexible, or not offering support. The orthopedic device solves the problem of areas of the device not providing proper support such as by providing areas of undesirable levels of restriction and/or elasticity at certain parts of a limb.

The orthopedic device may have restrictive cables, straps, and/or restrictive bands or regions integrated and/or attachable into the construction of the device to restrict and guide the joint. These restrictive cables, straps and/or restrictive bands may be formed from metallic yarns, fusible, textiles, thermoplastic fibers, elastics, or other suitable materials and elements. They may be knit or inlayed during construction of the fabric brace, or mounted externally of the brace; alternatively, they may be modular and attachable to the device or components thereof for each adaptation in initial installation and use. In an embodiment, the orthopedic device comprises straps that intersect at a location that is effective for treating pathologies such as osteoarthritis. The orthopedic device may further comprise tabs for assistance in donning/doffing the device.

The embodiments of the orthopedic device define a compliant yet comfortable garment, such as a sleeve or other article, arranged to biomechanically provide motion restriction/facilitation of a joint or body segment. The embodiments are preferably adjustable in functional capacity to match the biomechanical requirements of a user's treatment plan throughout rehabilitation. The orthopedic device includes various comfort factors to facilitate maximal compliance of the user over the duration of their treatment such as profile, breathability, compression, flexibility, and rigidity.

The orthopedic device may be provided with zones of different elasticity or devoid of elasticity, toughness, durability, and compressibility whereby the knitted structure of the orthopedic device has varying zones of compressibility serving as padding. The zones can be provided with other components, such as straps. For example, the orthopedic device may define at least two zones whereby the first zone has a more compressible knitted structure over which straps extends. In the second zone, the knitted structure may be thinner and more elastic than the first zone so as not inhibit movement of the orthopedic device about the user. Embodiments are provided with zones of differing elasticity to offer improved support and migration control over existing devices.

In certain embodiments, the orthopedic device comprises a patella pad with enhanced anti-migration properties that offers support to a patella region and overcomes the problems of existing patella supports by offering enhanced flexibility, pressure relief, and support areas. The anti-migration properties may include tackiness that inhibits slippage against either the orthopedic device or skin of a user, or may include a surface relief that provides traction. The surface relief may be arranged so as to facilitate breathability with gaps or channels along the surface relief.

Embodiments are provided to offer improved migration control over known devices. Embodiments may include means for removing or mitigating migration control during donning and doffing, while offering improved migration control during use.

In an exemplary embodiment, the migration control comprises a frictional material placed about and/or on the orthopedic device or in sections at a predetermined location or locations of the orthopedic device, such as a top or proximal end. The frictional material is preferably deposited along an inner surface of the orthopedic device. The frictional material may be arranged in a pattern to provide breathability but balance tackiness and friction against a user's skin with comfort. The orthopedic device is arranged with a cuff that bears the frictional material, and can be folded over the orthopedic device during donning and doffing to disengage the frictional material from the body of the user.

Upon reaching a desired location of the orthopedic device on the user, the cuff can be reverted to a position allowing for engagement of the frictional material to the body of the user. The orthopedic device may include appropriate markings or indicia to guide a user to the extent the orthopedic device is to be folded to facilitate donning and subsequent engagement of the frictional material against the skin of the user.

In these and other possible embodiments, the problems of orthopedic devices including flexible orthopedic devices and sleeves being ineffective at migration control and/or difficult to don/doff, offering ineffective patella support, and being ineffective at mitigating pathologies such as osteoarthritis, are addressed and mitigated.

BRIEF DESCRIPTION OF THE DRAWINGS

These and other features, aspects, and advantages of the present disclosure will become better understood regarding the following description, appended claims, and accompanying drawings.

FIG. 1A is a front elevational view of an embodiment of a knee support according to an orthopedic device.

FIG. 1B is a side elevational view of the embodiment of FIG. 1.

FIG. 2C is a perspective view of another material structure in an embodiment of an orthopedic device.

FIG. 2D is a detail view of the detail IID when the orthopedic device is in extension.

FIG. 2E is a detail view of the detail IID when the orthopedic device is in flexion.

In the figures, similar elements are provided with similar reference numbers. The drawing figures are not drawn to scale, or proportion, but instead are drawn to provide a better understanding of the components, and are not intended to be limiting in scope, but provide exemplary illustrations.

DETAILED DESCRIPTION OF VARIOUS EMBODIMENTS

A. Fabrication of Various Embodiments

Figure 2A:
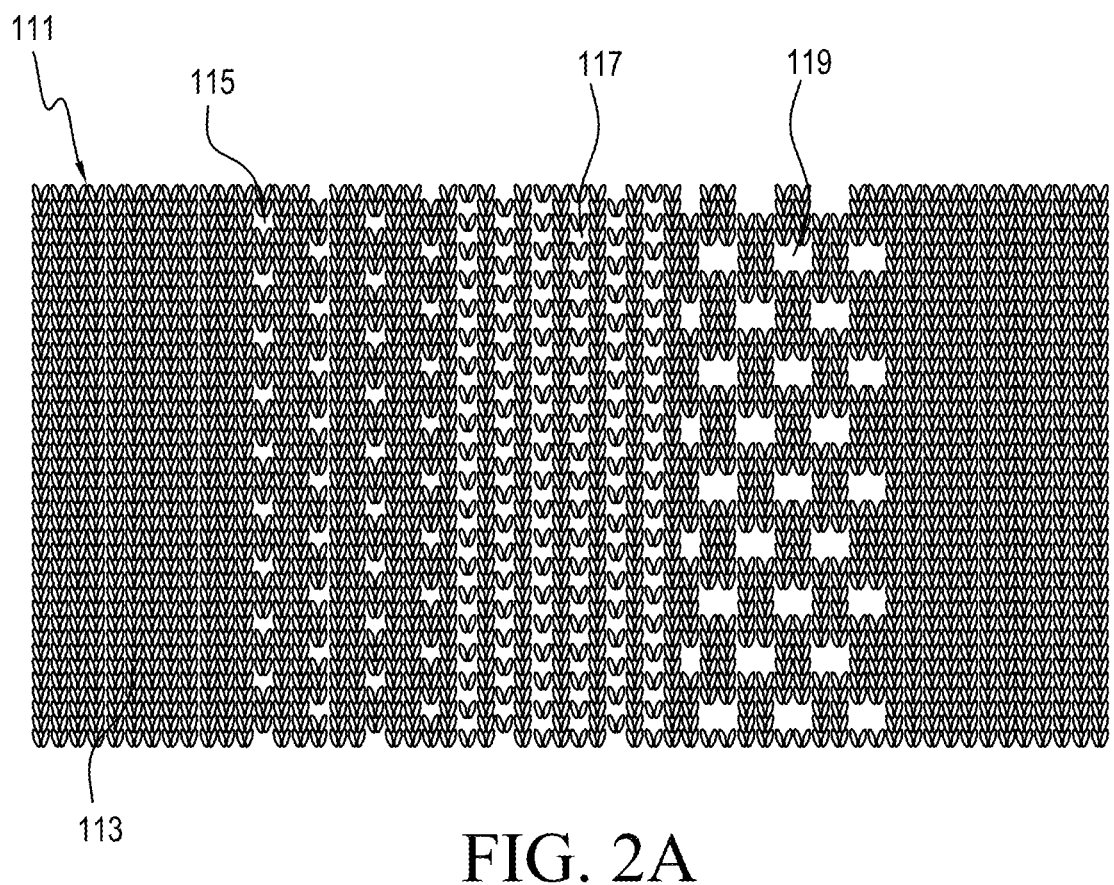
FIG. 2A is a detail view of a material structure in an embodiment of an orthopedic device.

Various embodiments of the orthopedic device may utilize flat knitting, which allows production of textile structures into a final desired shape so there is no cutting and very minimal waste. Flat knitted elements are formed directly in the desired three-dimensional shapes or modular panels, which can help avoid the need to use additional support structures.

In engineering the stitches to stretch, restrict, pad, or contour to body shapes, using multiple types of yarns and/or combined stitch patterns at strategic placements, several desired performance characteristics can be localized into performance zones within a single, unitary construction. Various pockets, channels, and tunnels can be formed by the knitting to introduce: restrictive stays, pads, hot/cold packs, hyper elastic materials, inflatable pouches (liquid or air), webbing, hardware, and/or other customizable elements of bracing and support. Inflatable areas in the knit pouches can exert pressure and force on the desired areas and are customized to a patient's condition.

Embodiments of the functional knit orthopedic device preferably form a knitted textile support having a shape created on a knitting loom including, but not limited to, various warp knitting, circular knitting, or weft (flat) knitting processes.

Embodiments of the functional knit orthopedic device may take the form of a garment. Support areas may include several textile elements combined into one textile support panel with unitary construction or a group of modular panels for treating a medical indication. The body of the textile panel or panels provides for biomechanical range of motion, compression, and therapeutic elements integrated into a single panel, or panels that may form a garment. Three-dimensional flat knitting allows production of these textile structures into a final desired shape to avoid cutting and waste.

Each panel or series of panels may have areas of gradient levels of stretch, flexure, rigidity, and restrictive elements integrated into the fabric by mapping the levels of motion or restriction required for a medical indication. This is achieved through a corresponding system of knit stitching techniques that start with yarns. Knit stitching techniques create varying degrees of elasticity, rigidity, open channels, tunnels, and intarsia zones of specialized yarns integrated into the base fabric. The first area of knitting may be formed of a first stitch configuration, and the second area may be formed of a second stitch configuration different from the first stitch configuration to impart varying textures or properties to a surface of the textile element. These properties may include anti-bacterial, cooling, warming, elasticity, rigidity, compression, wicking, and/or color.

The knitted base of the device can comprise natural and/or synthetic yarns: silk, wool, polyester, nylon, olefin, and interlaced with specialty yarns: moisture management, elasticized, fusible, metallic, Kevlar, silicone, and other types of performance yarns knit into fully fashioned, textured, intarsia, or three-dimensional regions and appendages such as connected tubes, circles, open cuboids, straps, spheres, and other integrated knit shapes.

Flat knitted elements may be formed directly in the desired three-dimensional shapes or modular panels, which can help avoid the need to use additional support structures and emerge from the machine ready to be sewn together, advantageously saving on manufacturing costs. This fully fashioned knitting technique adds or drops stitches to create custom two- and three-dimensional shapes appropriate to the desired finished garment structure.

The intarsia areas may comprise threads or yarns, which are isolated into specialized zones, using silicon, Kevlar, fusible, nylon monofilament, Dynema, spandex, and/or other specialty performance yarns knit into the fabric to enable that region to perform a function. These areas can be arranged into any flat, textured, or three-dimensional shape required for load mapping the garment for the medical indication.

The load mapped zones may be further achieved by combining knit structures (knit, tuck, miss), transferring loops, dropping or adding needles, segmenting takedown in varying rates across the width of the garment fabric, varying structural elements, inlaying yarns, weft insertion, direct feed, warp insertion, and varying speed of yarns fed into the system.

Besides standard knitting feeders, several types of specialized knitting feeders may isolate, apply, and integrate these yarns into the base fabric of this garment: intarsia feeders, in-lay, direct feeders, and plaiting feeders. With the plaiting, the yarn may lie in the isolated area but only on the face or the back of the fabric.

B. Biomechanics of Various Embodiments

Control of joint range of motion includes motion inhibition, restriction, or prevention. This may be obtained through altering tension in a garment on a tangent to the skin controlling motion through shear loads (at a tangent to the skin). Control of joint range of motion and soft tissue may be assisted through compression or loading, at or near a normal direction to the surface of the skin and/or garment.

In embodiments of the orthopedic device, normal motion may be disrupted by an intimately fitting garment with restrictive bands integrated therein for constructing the functional knit orthopedic device. The restriction may be created through altering both the yarn and the weave of the fabric. The interface between fabric and skin can vary. Some areas can be low stretch and have high friction or tackiness bonding the fabric to the skin. These regions form an anchor for stabilization of the garment to the core and the extremity.

Other textile areas can have high stretch and offer low friction, allowing the body segment to move freely. By carefully selecting the anchor zones and orienting restrictive bands within the textile, embodiments can provide restriction or guidance to the joint in question, preventing injurious movement and even encouraging safe motion strategies about the joint.

Some zones may serve to provide greater compressibility or padding than others, and may be arranged with components of the orthopedic device. For example, certain zones may have greater compressibility brought by the knitted structure or simply the physical structure, as in a greater thickness. These zones may have overlapping or integrated elements, as in straps, hinges, stays and other common brace components, whereby the zones of greater compressibility provide protection and comfort to the user by mitigating the exposure to the user of the components and their interaction to movement of the orthopedic device.

C. Definitions

Numerous orthopedic device embodiments and components for use therewith are described herein, with particular focus given to flexible orthopedic devices and/or sleeves, and components directed to joints, in particular the knee joint and surrounding areas. The orthopedic device embodiments may serve in protective, preventative, or remedial capacities. While the orthopedic device is described within the context of a preferred embodiment that is directed to the knee, many of the features described herein may be extended to various orthopedic devices and components that secure other joints and body parts. Other flexible orthopedic devices and sleeves may comprise sleeves and devices comprising neoprene and/or other textiles and materials, and may include other tubular configurations or other shapes and configurations as well.

The orthopedic device embodiments and components for use therewith may be dimensioned to accommodate different types, shapes, and sizes of human joints and appendages. In addition, embodiments may be modified to orient principal forces exerted by strap systems of the embodiments at any desirable location to secure the device onto a leg in order to stabilize the joint.

The knee joint comprises two joints, lateral and medial, between the femur and tibia, and one arthrodial joint between the patella and femur. The primary movements of the knee comprise flexion, i.e., rearward rotational movement of the tibia relative to the femur (the completion of flexion ideally resulting in a fully bent leg), and extension, i.e., forward rotational movement of the tibia relative to the femur (the completion of extension ideally resulting in a fully straightened leg).

For explanatory purposes, each orthopedic device embodiment or component thereof described herein may be divided into sections which are denoted by general anatomical terms for the human body. Such anatomical terms are provided to distinguish various elements of the device embodiments from one another, but which are not to be considered to limit the scope of the disclosure.

Each of these terms may be used in reference to a human leg, by way of example, which is divided in similar sections with a proximal-distal plane generally extending along the meniscus of the knee between the femur and tibia. The terms "proximal" and "distal" generally refer to locations of the device that correspond to the location of the leg relative to the point of attachment of the leg to the body. The terms "upper" and "lower" may be used in combination with "proximal" and "distal" to connote gradations in location of "proximal" and "distal." The location where the device corresponds to the knee joint is used herein to generally delimit the proximal and distal sections of the device.

The embodiments of the orthopedic device can also be considered to fall within "anterior" and "posterior" sections of an anterior-posterior plane. The anterior-posterior plane generally corresponds to the coronal or frontal plane of a human leg which lies along the central longitudinal axis of a body. A posterior side or element is therefore located behind this anterior-posterior plane, whereas an anterior side or element is located in front of the anterior-posterior plane.

The terms "inwardly" or "inner" commonly used herein to distinguish the side of the device that may be directed to the posterior side of the device and specifically adjacent to the leg of the wearer of the device. Contrariwise, the term "outwardly" or "outer" are used to denote the side of the device that is opposite to the inwardly side.

The terms "medial" and "lateral" are relative terms that are generally understood as indicating location with respect to the midsagittal plane or midline. Therefore, elements that are located near the midline are referred to as "medial" and those elements that are further from the midline are considered to be "lateral." The term "central" is used to denote the area along the midline of a joint thereby dividing and sharing regions of the medial and lateral regions.

The terms "rigid" and "flexible" may distinguish characteristics of portions of certain features of the orthopedic device. The term "rigid" should denote an element of the device is devoid of flexibility. Within the context of frame or support members or shells that are "rigid," it should indicate that they do not lose their overall shape when force is applied, and they may break if bent with sufficient force. The term "flexible" should denote that features are capable of repeated bending such that the features may be bent into retained shapes or the features retain no general shape, but continuously deform when force is applied.

D. Detailed Description of Various Embodiments

In any of the following embodiments, the features discussed with one embodiment may be extended to any of the other embodiments. The embodiments may include any of the features discussed in U.S. patent application Ser. No. 14/247,613, filed Apr. 8, 2014, and published as U.S. patent application publication no. 2014/0303534, published on Oct. 9, 2014, and incorporated by its entirety.

Referring to FIGS. 1A and 1B, an orthopedic device 100 is arranged as a knee support, in this particular embodiment as a functionally knit orthopedic device. While the embodiment in FIGS. 1A and 1B depicts a functionally knit orthopedic device, the teachings of the disclosure are equally applicable to other types of flexible orthopedic devices and orthopedic devices in general. The knee support 100 includes a main body panel or main panel or main body arranged in this embodiment as a knit tubular sleeve 101 having first and second regions 102, 104, 105 with different elasticities. The first and second regions 102, 104, 105 are continuously knit to one another to have a continuous structure without interruptions.

The first and second regions 102, 104, 105 are integrally knit to one another with the threads or yarns interwoven to one another rather than forming sections stitched to one another by additional threads or yarns. While integrally knit to one another, the first and second regions 102, 104, 105 may be considered discrete relative to one another because they are demarcated relative to one another by their properties, such as elasticity and/or color. Alternatively, the first and second regions 102, 104, 105 may gradually transition into one another due to sharing of certain properties of their knit, such as including shared elastic yarns. While in this embodiment the main body panel is arranged as a tubular sleeve 101, other configurations and shapes may be suitable.

A tension band 112 is integrally formed and functionally knit with the first and second regions 102, 104, 105. While the tension band 112 is functionally knit with the first and second regions 102, 104, 105 in this embodiment, tension band 112 may be adapted to be attached in any suitable way to other types of flexible orthopedic devices and orthopedic devices in general. The tension band 112 has a gradient region 114 dissipating into at least one of the first and second regions 102, 104, 105 to gradually taper into the first and second regions 102, 104, 105 toward first (proximal) and second (distal) ends 134, 136. Between the first and second ends 134, 136, the tension band 112 is preferably discrete in that it is clearly delineated from the first and second regions 102, 104, 105 without the dissipation. The tension band 112 may be arranged to extend about a patella region 108 of the knee support to improve support and tracking of the patella during physical activity.

The tension band 112 may lack or have minimal elasticity, such that it does not have or has only limited amounts of elastic yarns. Alternatively, the tension band 112 may be formed by yarns having more stiffness than yarns used to form the first and second regions 102, 104, 105.

The tubular sleeve 101 may define a third region 106 having a different elasticity than the first and second regions 102, 104, 105. The second region includes first (upper) and second (lower) portions 104, 105, preferably formed adjacent the first and second ends 134, 136, and operate as anchors to the dissipating portions 114 of the tension band 112. They may have a greater rigidity or elasticity than the first region 102, and may be on a medial or lateral side of the knee support 100. The third region 106 is preferably between the first and second portions 104, 105 to enable better bending of the knee support 100 in view of the greater rigidity of the first and second portions 104, 105.

The third region 106 includes a popliteal portion 126 and has a plurality of reinforcement bands 128 for modifying the flexibility of the popliteal portion 126. The first and third regions 102, 106 may have generally the same elasticity at certain portions thereof. According to the embodiment of FIGS. 1A and 1B, the third region 106 at the popliteal region 126 has a different elasticity than the first region 102 due to the reinforcement bands 128.

The patella region 108 is separate from the first and second regions 102, 104, 105. The patella region 108 forms an opening 110 and may have a panel 122 extending over the opening 110 to provide protection and proprioception for a user. The panel 122 may have elasticity greater than the first and second regions 102, 104, 105 so as not to inhibit bending of the patella. As an alternative, the panel 122 may have greater rigidity to restrict bending of the knee and offer enhanced support. The panel 122 may be continuously knit with the other features, or selectively removable from the tubular sleeve 101, such as from an inner surface of the orthopedic device 100.

The patella region 108 may have a bolster 116 formed around the opening 110 and protruding outwardly a distance 130 from a profile 132 of the tubular sleeve 101. The bolster 116 may include padding embedded within the tubular sleeve 101. The bolster 116 may taper toward the opening 110 and have a greater height away from the opening 110. The bolster 116 may have a variable outer radius extending from the opening 110. The bolster 116 may have a greater upper height 138 toward the first end 134 than a lower height 140 toward the second end 136 of the tubular sleeve 101. The bolster 116 may include padding and reinforce and protect the knee of a user while functioning in combination with the tension band 112 to provide support to the user's knee during gait.

The tubular sleeve 101 may have a circumferential band 118 arranged about an open first end portion 134 of the tubular sleeve. The circumferential band 118 may have different elasticity than the first and second regions 102, 104, 105, and preferably has significant elasticity with retaining properties functionally similar to a circumferential strap without the specific need for a strap to retain the knee support 100 on the leg of a user.

A binding 120 is provided about an open first end 134 of the tubular support 101 and terminates the circumferential band 118. The binding 120 terminates the knee support 100 at a peripheral edge and protects the fabric of the knee support 100 from unraveling or damage. The binding 120 may be integrally knit with the circumferential band 118.

A stay 124 is located between first and second ends 134, 136 of the tubular support 101 to provide support for articulation of a knee support 100. The stay 124 may be embedded within the tubular support 101 or may be formed by stiffer knit or a combination of a support element such as a plastic strip and unique knit for forming the stay 124.

FIG. 2A shows an exemplary knit structure 111 formed from a knit material or knitting 113. The knit structure 111 includes a plurality of apertures having different sizes 115, 117, 119 and formed from the knit material 113. A first set of apertures 115 is smaller than second and third sets of apertures 117, 119 and has less elasticity than the second and third sets of apertures 117, 119.

Figure 2B:
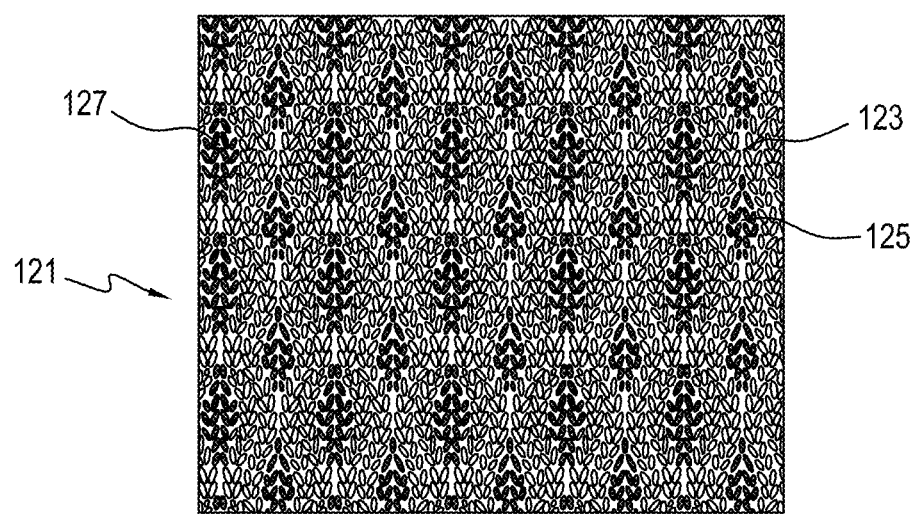
FIG. 2B is a detail view of another material structure in an embodiment of an orthopedic device.

FIG. 2B shows another exemplary knit structure 121 having a plurality of different knit patterns 123, 125, 127. A first knit pattern 123 surrounds a plurality of sections of second and third knit patterns 125, 127. The first knit pattern 123 may have different properties than the second and third knit pattern 125, 127. The first, second, and third knit patterns 123, 125, 127 may be distinguishable from one another on the basis of their color, elasticity, or a tightness of their knit.

FIG. 2C exemplifies another knit structure 141 in a knee support 100. In this embodiment, the knit structure 141 comprises different zones, such as first 142, second 143, and third 144 zones, that have different colors. Each zone 142, 143, 144 may have first and second layers of material 145, 146 (or outer and inner), which may be constructed from differently colored knitted structures, for example black and blue to obtain a visible contrast from each other.

For example, FIG. 2D shows the knee support 100 in extension whereby the first and second zones 142, 143 are not significantly tensioned over the knee. FIG. 2E shows the knee support 100 in flexion and tensioned or stretched over the knee whereby the contrast between the first and second zones 142, 143 is substantially more prominent due to a greater separation of discrete sections of the first layer 145, such as columns or rows of the first layer 145 of material, and the revealing of the knitted structure of the second layer 146 between the first knitted structure 141, in that one can easily observe a contrast between the first and second layers of material 145, 146, whereas the contrast of such first and second layers 145, 146 of knitted material in FIG. 2D is minimal or non-existent.

The contrast of the layers offers a "shine-through" effect that provides a more aesthetic appearance of the knee support 100, particularly as the knee support 100 undergoes tensioning and movement of the limb upon which it is worn. The shine-through effect offers a unique appearance to the knee support 100 that enables the manufacturer to distinguish its knee support 100 over other orthopedic devices. The contrast is not limited to colors of the knitted material, but can also relate to different finishes (stain, sheer, gloss) of the knitted material.

In this way, the first and second layers 145, 156 may further advantageously provide for different properties of moisture wicking, breathability, and heat transfer as required. For example, the first layer 145 may provide a tighter weave pattern to resist dirt and liquids from outside the orthopedic device to maintain cleanliness, while the second layer 146 may provide enhanced breathability for comfort. Alternatively, the first layer 145 may be configured to have less elasticity than the second layer 146, such that when the knee support 100 is bent in flexion, the first layer 145 provides enhanced compressed against the joint. Numerous advantageous arrangements of the first and second layers 145, 146 can be similarly envisioned.

Figure 3A:
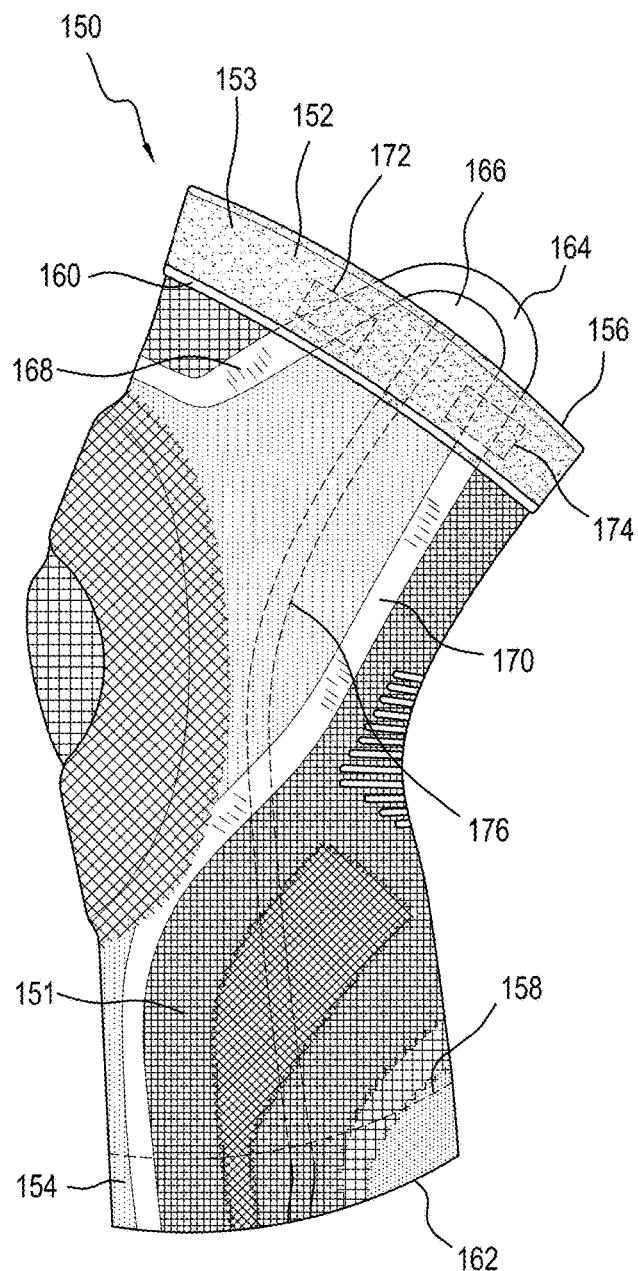
FIG. 3A is a side elevational view of another knee support according to an embodiment of an orthopedic device in a disengaged configuration.
Figure 3B:
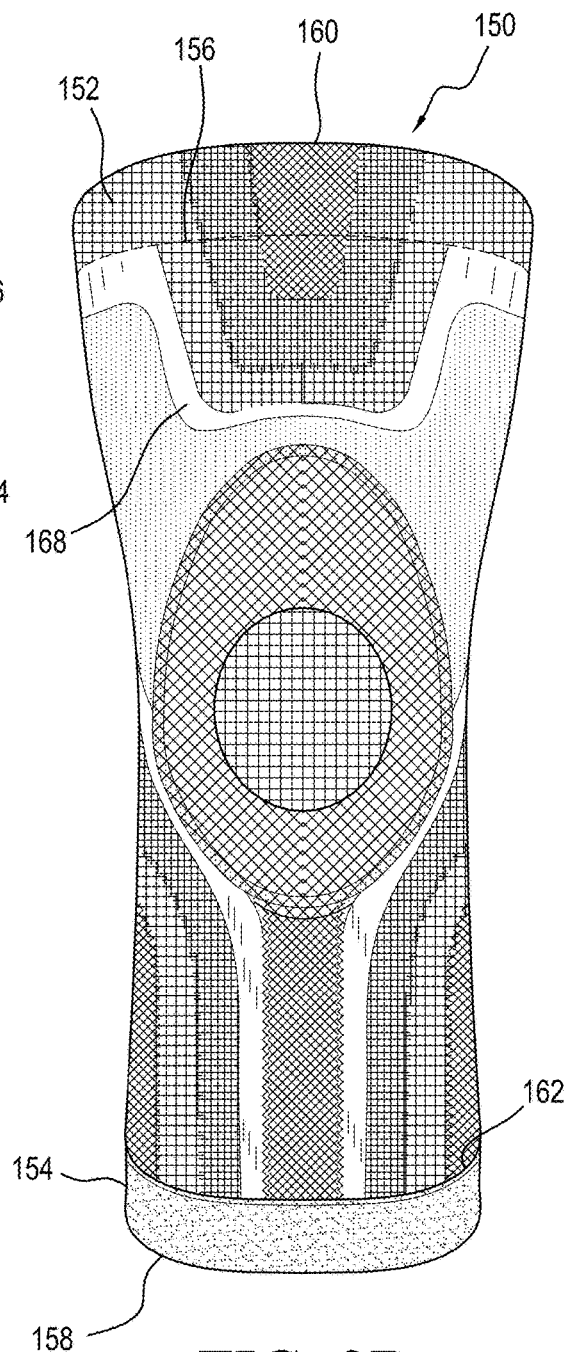
FIG. 3B is a front elevational view of the embodiment of FIG. 3A in an engaged configuration.

FIGS. 3A and 3B illustrate a variation of the orthopedic device of FIGS. 1A and 1B. In the orthopedic device 150, an upper cuff 152 is secured to a tubular body 151. The upper cuff 152 is arranged to provide migration control, which may be accomplished in a variety of ways, but is nonetheless to be disengaged during donning, doffing, and fitting of the orthopedic device 150 such that the orthopedic device 150 may be easily donned or doffed without sacrificing the advantages of the migration control.

In the illustrated example, the upper cuff 152 defines a frictional surface by use of a frictional material 153 that is arranged to engage the skin of the wearer and maintain the tubular sleeve 151 on the leg. An example of the frictional material 153 is silicone that is applied to an inner surface of the cuff 152 (when engaging the skin). Alternatively, the upper cuff 152 may be arranged or suitably knit in a manner that provides radial compressive forces about the leg.

The upper cuff 152 is adapted to flip over an upper end portion of the tubular sleeve 151 during donning. For example, upper cuff 152 defines a first edge 160 which forms an upper edge to the orthopedic device 150 when the upper cuff 152 is in an engaged configuration for normal use (as in FIG. 3B), and the first edge 160 is arranged to flip over the tubular sleeve 151 when the upper cuff 152 is in a donning/doffing or disengaged configuration (as in FIG. 3A). A folding portion 156 forms a joint about which the upper cuff 152 folds over the tubular sleeve 151, and generally demarcates where the frictional material 153 terminates. The upper cuff 152 is arranged such that when the upper cuff 152 is folded over the tubular sleeve 151, the upper cuff 152 is adjacently against the tubular sleeve 151, wherein an outer surface of the upper cuff 152 snugly abuts a portion of an outer surface of the tubular sleeve 151 due to its radially compressive construction.

The orthopedic device 150 may include a lower cuff 154 arranged similarly to the upper cuff 152, for migration control of the orthopedic device 150 when in an engaged configuration. The lower cuff 154 may include a frictional material, and is arranged to flip over the tubular sleeve 151 about folding portion 158. When in an engaged configuration, the first edge 162 of the lower cuff 154 forms a lower edge of the orthopedic device 150. When in a disengaged configuration, the folding portion 158 forms a lower edge of the orthopedic device 150.

In order to facilitate donning of the orthopedic device 150, handles or pull tabs 164 may be provided so as to extend from the tubular sleeve 151 to assist in pulling the orthopedic device 150 about a leg. As the knitted structure of the tubular sleeve 151 is intended to snugly secure about the leg, and in view of the need to tension the orthopedic device 150 about differing circumferences of the leg, the handles 164 enable the user to position the orthopedic device 150 in a suitable location to maximize the benefit of the orthopedic device 150. The handles 164 may include an opening 166 for insertion of fingers to aid the user in gripping the handles 164, which is particularly advantageous when the user is infirm or there are significant circumference differences of the user's leg, as handles 164 offer a user better purchase than trying to grip the tubular sleeve 151.

The handles 164 also advantageously prevent a user from pulling directly on the tubular sleeve 151, thus preventing damage thereto. Pulling on handles 164 rather than tubular sleeve 151 is also more intuitive and simple for users, as doing so is less likely to result in undesired rotation of the orthopedic device 150 during donning. By locating the handles 164 on an inner surface of the tubular sleeve 151, damage is averted as the handles 164 are less likely to accidentally catch on objects as a user moves about, and the upper cuff 152 is better able to fold over the tubular sleeve 151 for donning and doffing without interfering with the use of the handles 164.

The tubular sleeve 151 may define band segments 168, 170 that are reinforced or have an elasticity or omit elasticity in line with the contours of the handles 164. For example, the band segments 168, 170 are inelastic or substantially inelastic so the tubular sleeve 151 can be suitably, sufficiently, and generally uniformly tensioned about the leg, as it is readily understood from the other embodiments described herein that there are elastic and flexible regions belonging to the orthopedic device 150.

The handles 164 may be extensions of the knitted band segments 168, 170 and may flexibly extend from the tubular sleeve 151, or alternatively may be secured to the tubular sleeve 151 such as along the upper folding portion 160. In a variation, as depicted in FIG. 3A, the handles 164 may be slidably mounted to the tubular sleeve 151 by internal loops 172, 174 on the tubular sleeve 151. When not in use, the handles 164 may retract relative to the tubular sleeve 151, and when desired for use, the handles 164 can be extended relative to the tubular sleeve 151. Particularly, if an upper cuff 152 is not provided with the orthopedic device 150, the handles 164 can still be used for donning the orthopedic device 150.

The orthopedic device 150 includes a stay 176 generally formed by reinforced knitting on the tubular sleeve 151. The stay 176 may be knitted over the tubular sleeve 151 by different, stiffer and resilient yarns or a combination thereof, or may be knitted together with the remainder of the tubular sleeve 151.

The orthopedic device 150 omits features in a region directly adjacent to upper cuff 152 such that upper cuff 152 can be folded over to be adjacently against tubular sleeve 151 without interference from other features, such as straps, buckles, tightening devices, or otherwise.

Figures 4A, 4B:
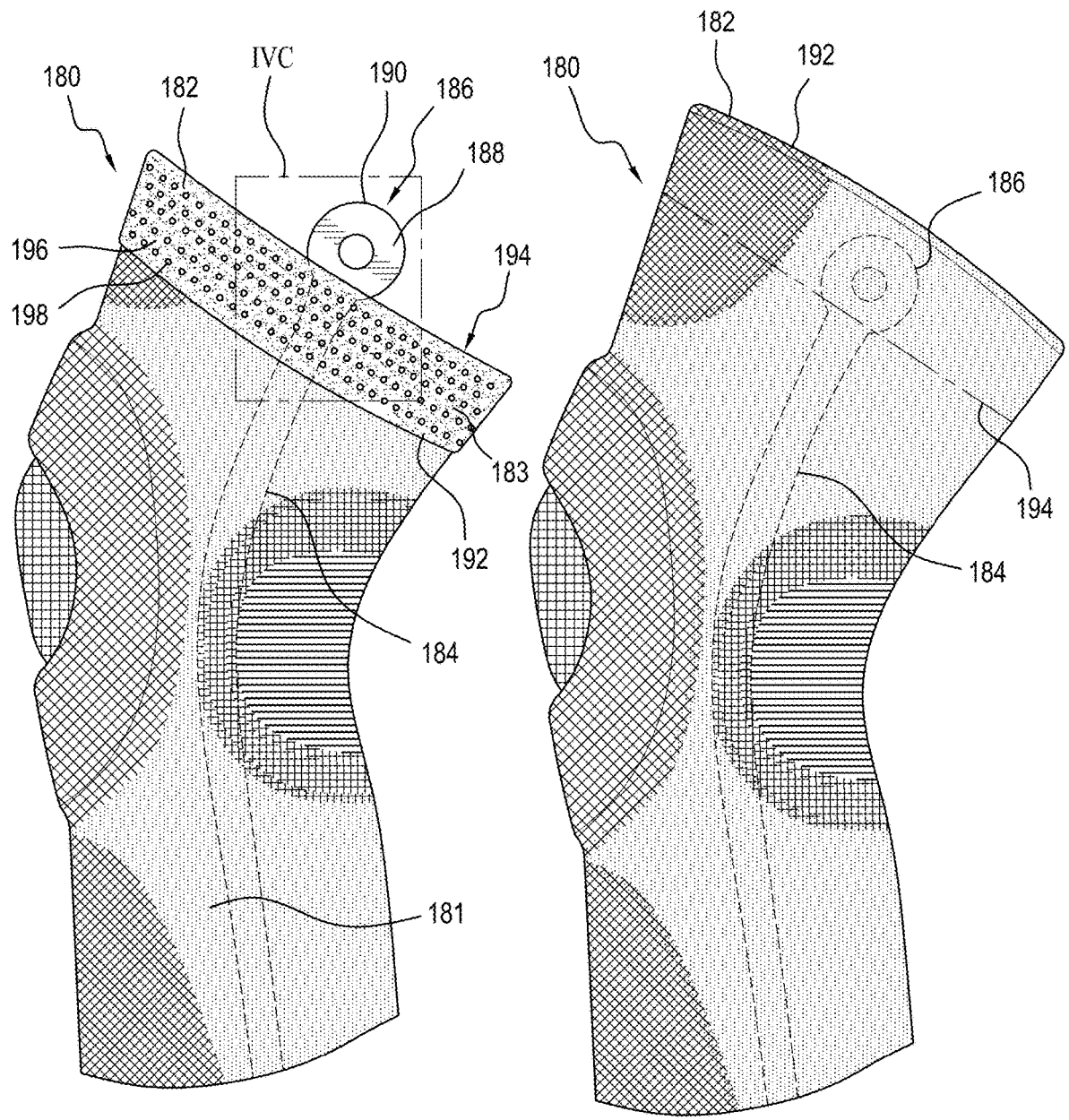
FIG. 4A is a side elevational view of another knee support according to an embodiment of an orthopedic device in a disengaged configuration.
FIG. 4B is a front elevational view of the embodiment of FIG. 3A in an engaged configuration.

FIGS. 4A and 4B represent another embodiment of an orthopedic device 180 having an upper cuff 182 in combination with a resilient stay 184 that is provided in combination with a main body panel arranged in this embodiment as a tubular sleeve 181. In this embodiment, the upper cuff 182 includes a frictional material 183 located on a surface thereof and arranged to engage the skin of the user similarly to the embodiment of FIGS. 3A and 3B. The stay 184 is formed by plastic or metal and has resilient properties adapted to resisting flexion of the orthopedic device 180, and extends between upper and lower ends of the orthopedic device 180. The stay 184 incorporates at its upper end a handle 186 that is integrated therewith. The handle 186 includes a head portion 188 configured for facilitating grasping with padding 190 located along a surface of the handle 186 adjacent the user's skin.

By incorporating the handle 186 with the stay 184, preferably on medial and lateral sides of the orthopedic device 180, rotation of the orthopedic device 180 about the user's leg can be prevented during donning. Indeed, once the upper cuff 182 is flipped about an upper folding portion 194 into an engaged configuration with an upper cuff edge 192 forming the upper edge of the orthopedic device 180, the upper cuff 182 prevents migration and rotation of the orthopedic device 180 on the leg. Contrariwise, when the upper cuff 182 is in a disengaged configuration, the upper cuff 182 is folded over tubular sleeve 181 so as to be adjacently against the tubular sleeve 181, due to the upper cuff 182 having radially compressive properties. In this configuration, an outer surface of the upper cuff 182 snugly surrounds a portion of the outer surface of the tubular sleeve 181, which is possible due to other features of the orthopedic device 180 being spaced downwardly from the upper cuff 182.

The frictional material 183 may be provided in different forms. In the example of FIG. 4A, the frictional material 183 defines a band 196 that generally circumferentially extends about the inner surface of the upper cuff 182. The band 196 may include a texture 198 that may form a plurality of openings, raised surfaces, random texture, or other textures that improve comfort for the user. In the embodiment of FIG. 4A, a preferred frictional material 183 is silicone, in part due to its skin adhering properties and it enabling gentle roll-off when doffing the orthopedic brace 180 and therefore folding the upper cuff 182 over the tubular sleeve 181. Other materials are envisioned providing similar properties.

In an alternative embodiment, the cuffs in the aforementioned embodiments may be formed by knitted silicone. As silicone has skin tackiness properties enabling gentle roll-off and roll-on, while having proven migration control characteristics, any of the embodiments may include silicone knit regions, whether by intarsia, terry stitch, waffle, circumferential areas, or other suitable applications. An example of silicone knitting is discussed in U.S. patent application Ser. No. 15/219,772, filed on Jul. 26, 2016, and incorporated herein by reference.

Uses of the knitted silicone include suspension, as in the aforementioned embodiments, massaging effects, and capture of bony and muscle anatomies. For suspension the knitted silicone may be at the top and/or bottom of a tubular brace, as in the upper and lower cuffs. The knitted silicone may be located along the length of the tubular brace, in which case it is best to have it in the same plane as the bending of the joint occurs, where shortening/lengthening does not occur. For example, in the knee, this would be along the medial and lateral side.

In another use of knitted silicone, the knitted silicone areas may provide a massaging effect, such as around the Achilles tendon, in the case of Achilles tendonitis. Silicone knit areas can be used for massaging, as the silicone knit areas are soft and do not exert any painful pressure, while evenly distributing pressure. The massaging effect may be provided by intarsia or terry knit in desired areas of the orthopedic device, while increasing in grade of an area to increase blood flow.

The knitted silicone can be arranged for capturing key bony anatomies through the surface of the skin. The silicone area can capture, for example, the patella of the knee by relying on the compression and frictional features and localizing the silicone area about the patella.

The knitted silicone can be used to capture key anatomies, and can be knitted into the orthopedic device to take place of Kinesio-taping or as elastic therapeutic tape built into the knitted structure of the orthopedic device as a whole. For example, in the embodiments described herein, one of the zones or regions of different elasticity may include a zone or region that is formed by knitted silicone so as to stretch beyond the original length of the zone to create a pulling force on the skin by the frictional properties and recoiling of the knitted silicone zone when the orthopedic device is worn. Thus, knitted silicone zone can be pretensioned or otherwise modified to create traction or pulling forces on the skin in combination with its adhesive properties.

As understood in Kinesio-taping applications, the knitted silicone zones may have general shapes for different taping type uses. For example, an "I" shape may be used for small or linear places, a "Y" shape may be employed for larger muscles, and an "X" shape may be used for long and large muscles.

Knitting in silicone presents two major challenges: first, the silicone is very sticky, and second, the silicone is highly elastic. Taken together, these challenges make it difficult to knit with silicone. The reason is that when knitting, the stickiness of the silicone causes it to stretch greatly in an uncontrolled manner. Since yarn stretch is crucial to form when knitting, the finished product will be greatly variable, and the manufacturing unreliable. To prevent this, one can either limit the elasticity of the silicone or make it less sticky.

One way to limit the elasticity of the silicone is to extrude it around a nylon core. The nylon core fabric can be spun in such a way as to have elasticity ranging from 0% (completely inelastic) to 100% (able to stretch to double its length at rest) or beyond. This method permanently limits the elasticity of the silicone yarn.

Another way to limit the stickiness of the silicone is to spin a non-sticky yarn around the silicone core. The silicone yarn can then be freely knitted. The external yarn is then removed post-knitting, for example by dissolving it in hot water or through some chemical process. In this method, the silicone retains its stickiness and elasticity.

Yet another way of limiting the stickiness of the silicone is to coat it in an oil or non-sticky powder prior to knitting. This will reduce the stickiness of the silicone. However, like the previous method, the oil/powder coating will need to be removed post-knitting. Possibly, the method of removal may be as simple as washing the product in a washing machine.

As discussed above, parts of the orthopedic device can be knitted with silicone. This can be done in intarsia, where certain areas will then include silicone for functional benefits. This can also be done not in intarsia but in circumferential zones such as at the top and bottom edges.

The silicone knit can be done with multiple types of knit stitches. One stich type may result in the silicone creating a relatively uniform area of contact. It may be beneficial to have only limited contact with silicone, so another stitch may only expose part of the silicone yarn, and create "dots" of silicone in the garment. It may also be beneficial to have as much contact with silicone as possible, so to create larger surface area, the stitch may be a so-called "terry" stitch.

Figure 4C:
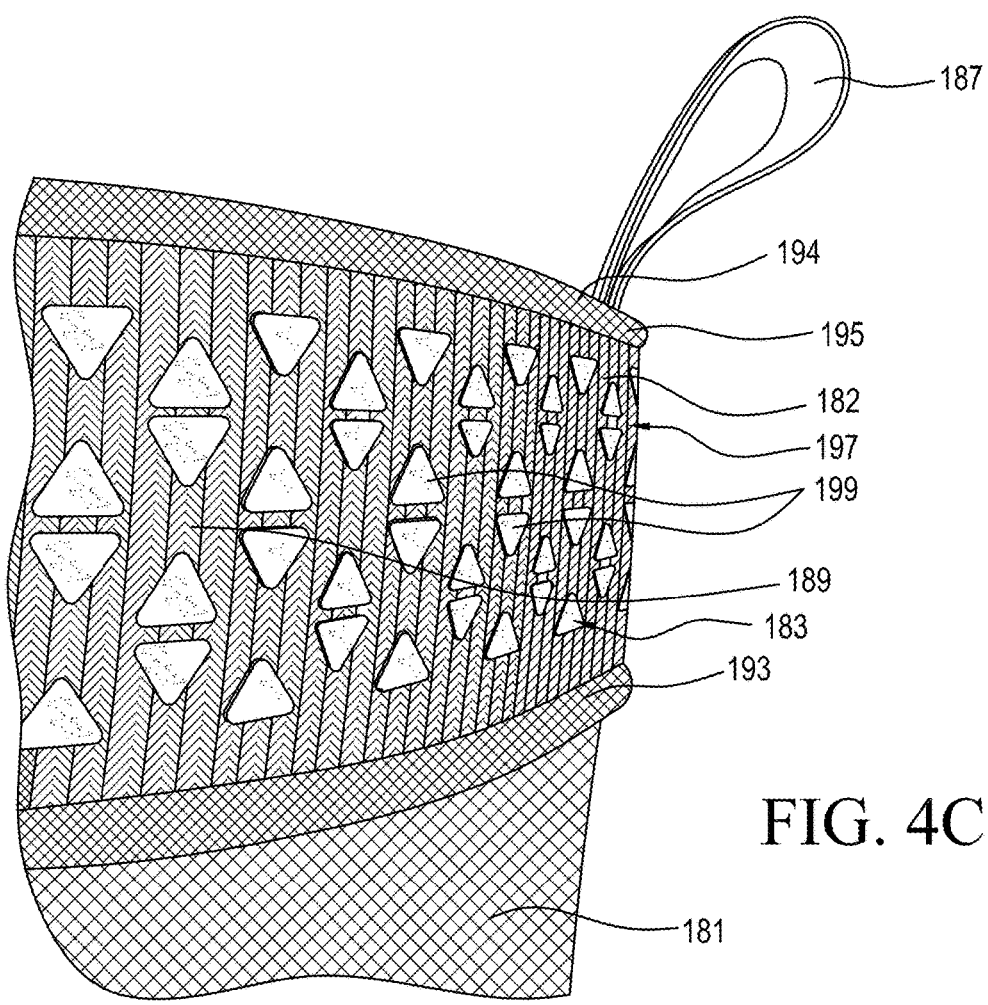
FIG. 4C is a schematic view of the embodiment of FIG. 4A showing a variation of an upper cuff in a disengaged configuration.

FIG. 4C exemplifies a variation of the upper cuff 182 in the folded or disengaged configuration, as in FIG. 4A. In this embodiment, the handle 186 is a flexible loop 187 stitched generally along the upper folding portion 194, or a distance into and along an interior side of the cuff, as in FIG. 9, so the loop only minimally extends from the orthopedic device when the cuff is not folded. In certain embodiments, the loop 187 is arranged such that when the upper cuff 182 is in the engaged configuration, the loop 187 is completely concealed by the upper cuff 182. A lower band 195 may be stitched or otherwise formed proximate the upper folding portion 194 to demarcate or delimit the folding of the upper cuff 182. Lower band 195 and upper folding portion 194 advantageously function to signal to a user where the upper cuff 182 is to be folded, so that the upper cuff 182 and the attached frictional material 183 are (preferably) adequately and completely disengaged from the user's leg when folded over. The loop 187 may be anchored along or proximate the lower band 195, and is preferably, but not limited, to being inelastic when pulled.

The upper cuff 182 has an upper band 193 that may have greater elasticity and reinforcement so as to apply greater circumferential pressure along a limb than the remainder of the upper cuff 182 or tubular sleeve 181. For example, the upper band 193 may be provided with more elastic elements when knitted, may have a tighter knitted structure, or may have a thicker knitted structure. Additionally, the upper band 193 advantageously allows an outer surface of the upper cuff 182 to be adjacently against an outer surface of the tubular sleeve 181 when in the disengaged configuration, in that the upper band 193 may assist the outer surface of the upper cuff 182 to snugly abut or surround a portion of the outer surface of the tubular sleeve 181 when folded over, in part due to the radial compression of the upper cuff 182 and in particular the upper band 193. The lower band 195 may likewise be modified to have a different knitted structure to facilitate folding and demarcating the extent of the folding of the upper cuff 182 over the tubular sleeve 181.

To further facilitate the folding of the upper cuff 182 into the disengaged configuration, or otherwise the extent to which the upper cuff 182 is folded over the main body of the tubular sleeve 181, at least an interior surface 197 of the upper cuff 182 may have a different color or knitted pattern than the tubular 181; for example, the tubular sleeve 181 may be black whereas the interior surface 197 is light blue.

While an upper cuff 182 is described, a lower cuff may be similarly structured in order to facilitate donning and doffing; that is, the lower cuff may likewise comprise bands specially configured to facilitate folding and demarcating the extent of the folding of the lower cuff over the tubular sleeve 181 in order to engage and disengage frictional elements. By configuring either or both of an upper cuff and a lower cuff to be engaged or disengaged at will by a user to facilitate donning/doffing of the orthopedic device, a key setback in orthopedic devices is overcome: the orthopedic device is able to be easily donned and doffed due to the disengaged configuration (wherein the frictional elements along the upper and lower cuffs do not abut the user's anatomy), but in the engaged configuration the frictional elements overcome the tendency of such devices to migrate along a user's leg, which tendency hinders the effectiveness of the device.

The interior surface 197 includes a frictional material 191 arranged in a pattern to balance friction between the upper cuff 182 and the intended limb of the wearer of the knee support with comfort and breathability for a user. For example, the frictional material 191 has a pattern of a circumferential array of discretely deposited sections 199 that are shaped to coincide of the knitted structure of the upper cuff knitted pattern 189. In this example, the frictional material pattern is similar to columns of opposing triangles that generally follow columnar aspects of the knitted pattern 189. In this example, the sections 199 are arranged so as not to impede breathability. The columns of the pattern of deposited sections 199 extend circumferentially about the interior surface 197 of the upper cuff 182, leaving sufficient space between each column to ensure breathability and comfort by balancing the exposure of the knitted structure and frictional material 191 against the skin of the user.

In this manner, the anti-migration properties provided by the frictional material 183 does not impede the breathability and consequently the comfort of the device, as with many existing flexible orthopedic devices which sacrifice comfort and breathability for better grip.

While the frictional material 191 is shown as having a pattern that generally corresponds to the knitted structure of the upper cuff 182, at least along the interior surface 197 thereof, the frictional material 191 may be provided in a pattern that does not correspond to the knitted structure.

Figure 4D:
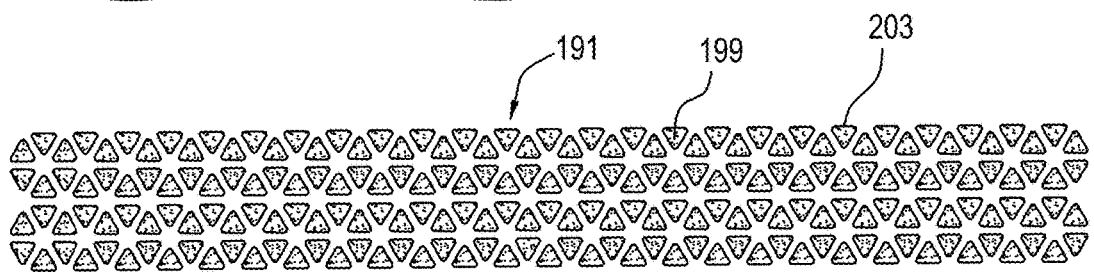
FIG. 4D is a schematic view showing a frictional material pattern.

FIG. 4D exemplifies a band 203 that can serve as a frictional material 191 that is deposited along the interior surface 197 of the upper cuff 182 of FIG. 4C. The pattern of the frictional material 191 may or may not correspond to the upper cuff knitted pattern 189. The band 203 may be formed separately from the knitted structure, and later applied to the interior surface 197 of the upper cuff 182, whether or not corresponding to the pattern 189 of the knitted structure. The band 203 has sufficient spacing among discrete regions to ensure sufficient breathability for the user in that the pattern is arranged so as to generally universally correspond to knitted structures while not substantially impeding airflow.

Figure 4E:
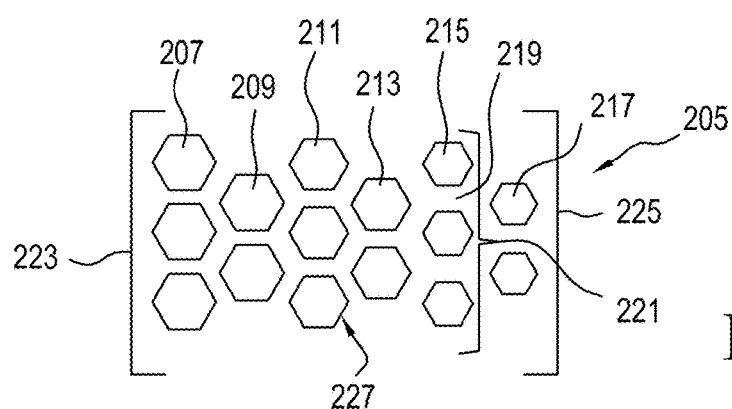
FIG. 4E is a schematic view of a variation of a frictional material pattern.

FIG. 4E is another example of a pattern 205 of frictional material. In this example, the pattern 205 defines a plurality of columns 207, 209, 211, 213, 215, 217 of discrete frictional elements 227. In this embodiment, the pattern 205 has boundaries 223, 225 within which the pattern 205 is located, which lends itself to being applied only to discrete segments of a circumference of the upper cuff 182. Alternatively, as in a cuff, the pattern may be provided to circumferentially extend about a cuff. In a preferred embodiment, the pattern 205 of frictional elements 227 comprises and/or is constructed of a knitted silicone or other tacky type thread.

The frictional elements 227 may be variably sized relative to one another in each column, and may comprise different spacings 219, 221 relative to one another, particularly if the pattern 205 is located on areas of an orthopedic device 200, not just an upper or lower cuff, that require variable friction. The spacings 219, 221 may facilitate better air passage so that a user does not significantly sweat and cause slippage of the frictional elements. As the frictional elements may be formed from a hydrophobic material, such as silicone, it is helpful to minimize discomfort to the user and migration of the frictional elements by providing means for enhancing breathability, as in providing spacings.

The spacings also enable greater surface area of the frictional elements for improved traction, as opposed to merely circumferential rings or threads with frictional material. The greater surface area of the frictional elements distributes resistive forces between the frictional elements and the user's skin in a more comfortable manner. Areas of greater need for frictional control, the frictional elements 227 may be larger and/or located closer to one another, and in areas with less need for frictional control the frictional elements may be smaller and spaced apart greater. In any situation, however, the variability of the pattern 205 may be adapted to variable frictional and migration control needs in an orthopedic device.

Even though frictional material may be contained in a cuff, of the type described above, it is often desirable for additional circumferential frictional control to prevent migration of the knee support on the leg of the user. Certain areas of the leg will lend themselves to including more migration control than others; for example, the anterior and posterior sides of the leg may require more frictional control, particularly in flexion and extension, than the medial and lateral sides of the leg.

Figure 5:
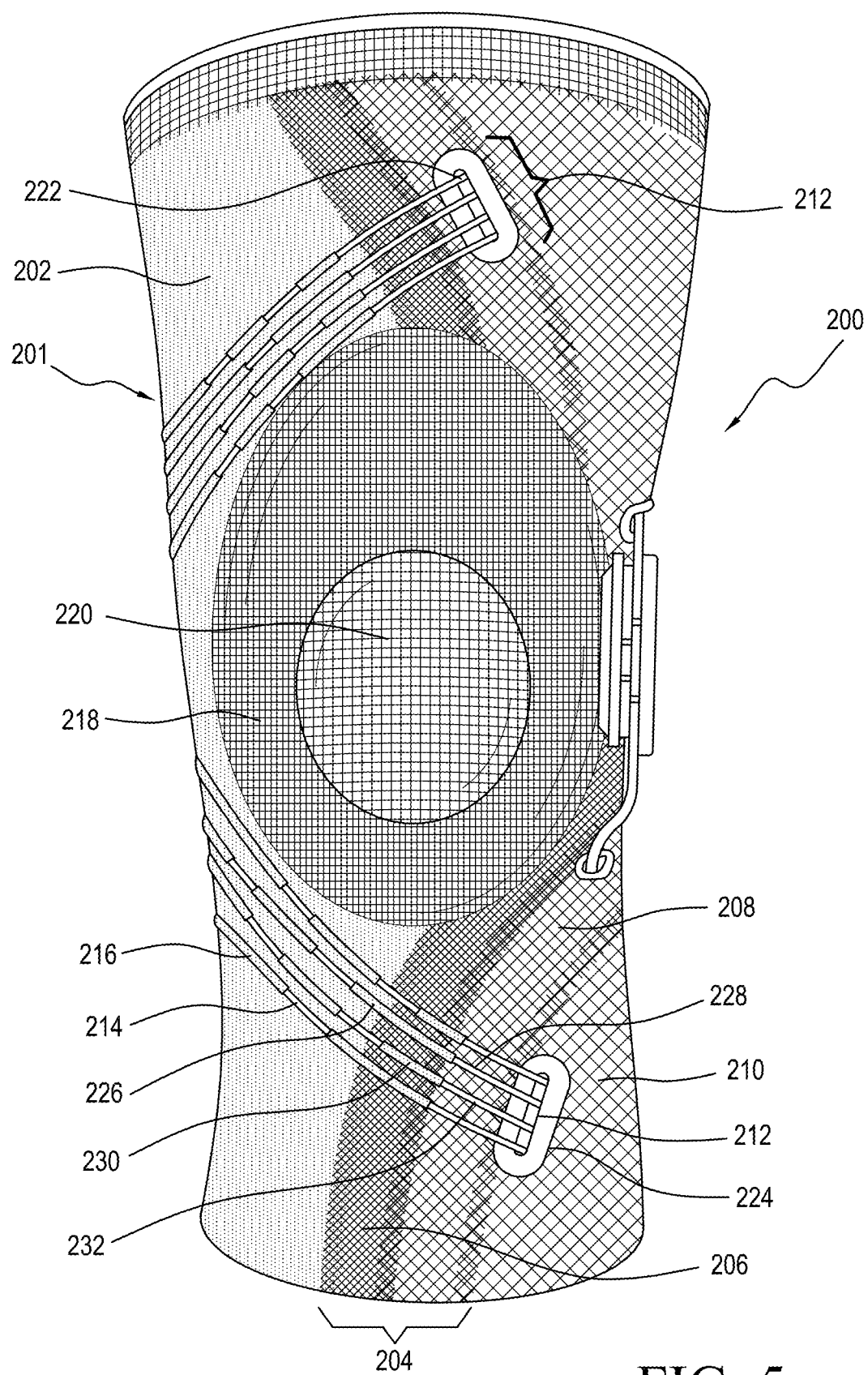
FIG. 5 is a front elevational view of another embodiment of a knee support according to an embodiment of an orthopedic device.

In another embodiment depicted in FIG. 5, an orthopedic device 200 in a knee support includes a main body panel arranged in this embodiment as a knit tubular sleeve 201 having first and second regions 202, 204 with different elasticities. The first and second regions 202, 204 are continuously knit to one another. The second region 204 includes at least first and second gradient segments 206, 208 arranged for modifying elasticity of the tubular sleeve 201 from the first region 202. The knee support 200 may include a third region 210 having different elasticity from the first and second regions 202, 204, and may resemble the first and second portions 104, 105 of the embodiment of FIGS. 1A and 1B.

The knee support 200 may include a patella region 218 defining an opening 220 in that each of the first and the second regions 202, 204 extends discretely about at least a portion of the patella region 218. The patella region 218 may resemble the patella region 108 of the knee support 100 of FIGS. 1A and 1B.

The knee support 200 includes a cable system 212 having at least one cable 214 slidably movable relative to the tubular sleeve 201. At least one guide 216 may be integrally formed from the tubular sleeve 201 and is arranged for receiving the at least one cable 214 such that the at least one cable 214 slides within the at least one guide 216.

In the embodiment, the cable system 212 is on an opposite side of the patella region as the first region 202. The second region 204, whether with or without the gradient 206, 208, and the cable system 212 may interact with one another and may be tailored or adjusted to offer the requisite support for a user's patella.

The cable system 212 may include an adjustment system (not shown) that enables tensioning of the cable system 212. Examples of adjustment systems may be found in U.S. patent application publication no. 2014/0303534, U.S. patent application publication no. 2013/0211304, published on Aug. 15, 2013, U.S. 2015/0032041, published on Jan. 29, 2015, and U.S. patent application publication no. 2015/0121657, published on May 7, 2015, each being incorporated herein by reference.

A slot 222 in the tubular support 201 is arranged for receiving a segment of the at least one cable 214. The at least one cable 214 is configured to have a segment received within a thickness of the tubular sleeve 201, and the adjustment system may take up or dispense a length of the at least one cable 214. The slot 222 may be reinforced with a reinforcement element 224 secured to the tubular sleeve 201 about the slot 222.

The cable system 212 preferably includes a plurality of cables 214 slidable relative to the tubular sleeve 201. A plurality of guides 216 are secured to a surface of the tubular support 201 and each is arranged for receiving an individual one of the cables 214. First and second guides 226, 230 may each be along a different segment of first and second cables 228, 232, and the first and second guides 226, 230 may have different lengths. The cable system 212 is preferably configured in a predetermined configuration over a surface of the tubular support 201 such that the at least one cable 214 is constrained in location over the tubular support 201 by the at least one guide 216.

The cable system 212 solves the problem of straps being difficult to use or adjust, and being cumbersome due to the straps straying from their intended location, tangling, or being damaged by external forces. By providing the cable system 212 with at least one cable 214 and at least one guide 216 defined by and/or integral with the tubular sleeve 201, the problems of straps are avoided but the beneficial purposes thereof (i.e. compression in specific locations, unloading of joints, securely mounting the device on the limb) may be retained.

Figure 6A:
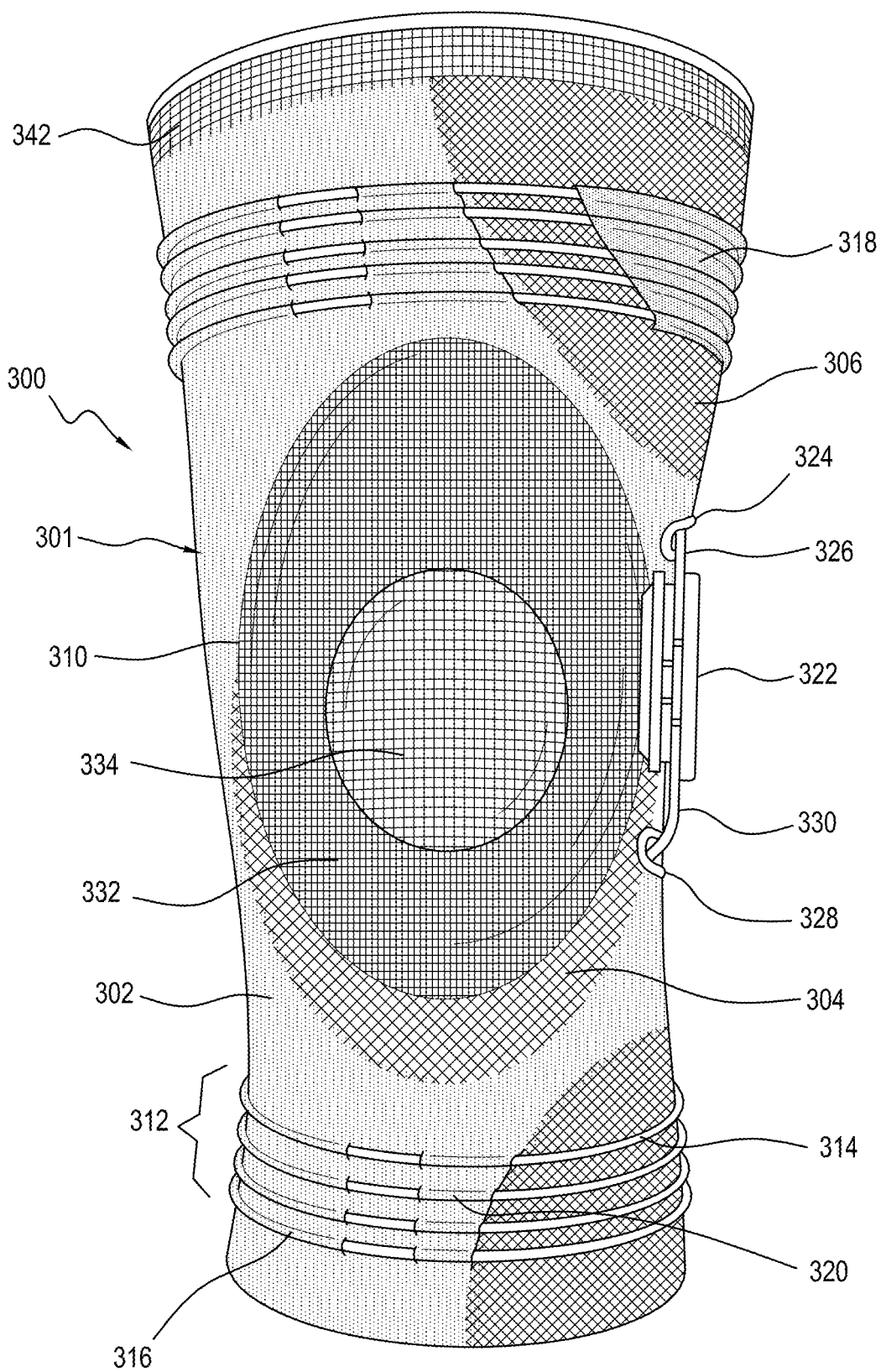
FIG. 6A is a front elevational view of another embodiment of a knee support according to an embodiment of an orthopedic device.
Figure 6B:
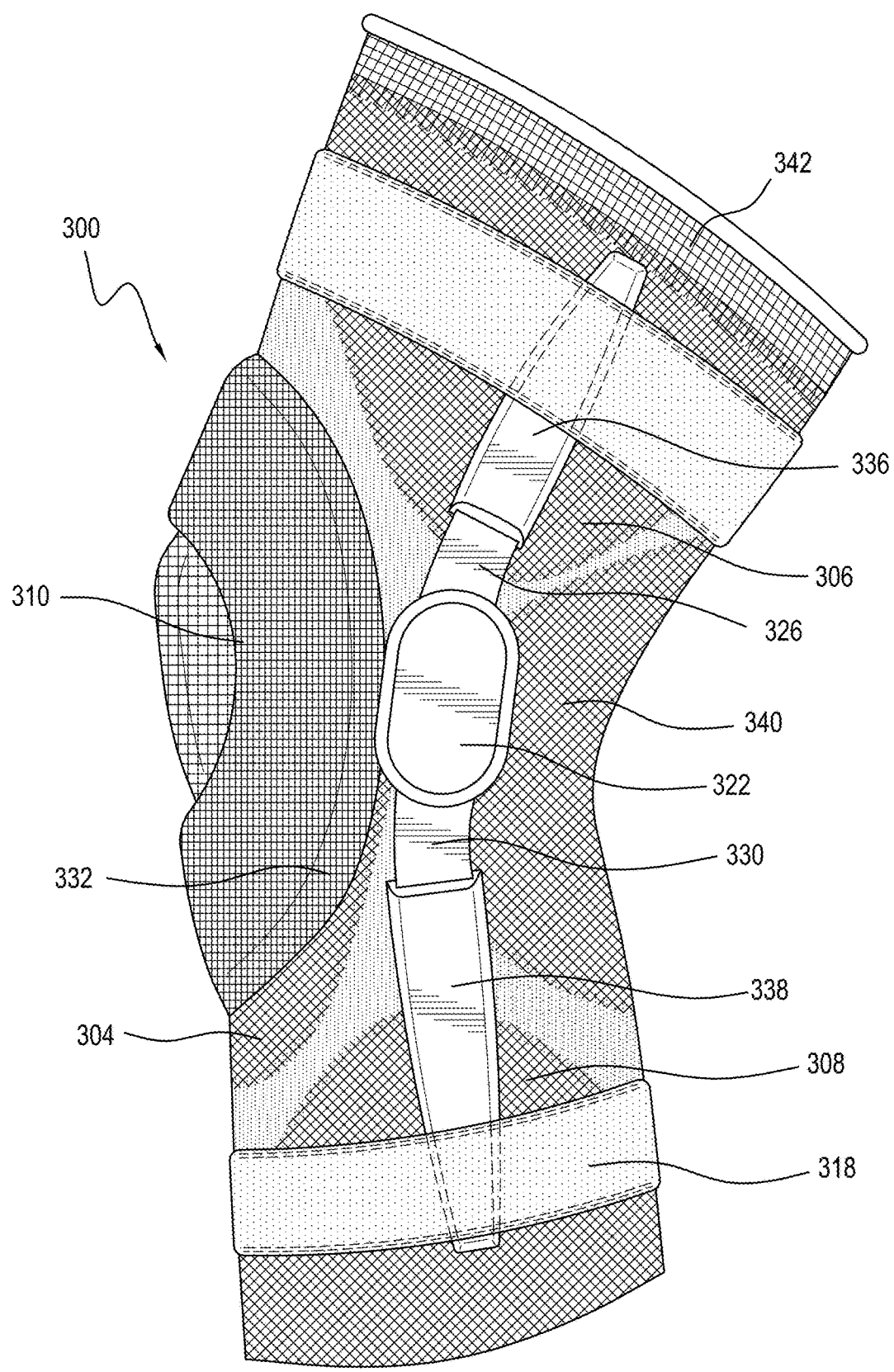
FIG. 6B is a side elevational view of the embodiment of FIG. 6A.

FIGS. 6A and 6B illustrate another orthopedic device embodiment in a knee support 300. As with foregoing embodiments, the knee support 300 includes a main body panel arranged in this embodiment as a knit tubular sleeve 301 having first and second regions 302, 304 with different elasticities. The knee support 300 has a patella region 310 defining an opening 334, with each of the first and the second regions 302, 304 extending discretely about at least a portion of the patella region 310. A bolster 332 is formed around the opening 310, and the second region 304 extends from the bolster 332 toward an end portion of the tubular sleeve 301.

The knee support 300 further has a hinge assembly 322 secured to the tubular support 301. To accommodate the hinge assembly 322, the tubular support 301 has first and second strut inserts 336, 338 secured to the tubular sleeve 301. The hinge assembly 322 has first and second struts 326, 330 received by the first and second strut inserts 336, 338. The strut inserts 336, 338 may be formed from a plastic material and laminated or stitched to the tubular support 301, being disposed along an external surface of the tubular support 301. The struts 326, 330 may be removable from the inserts 336, 338, and the inserts 336, 338 offer selective placement of a desired hinge assembly 322.

In a variation of the hinge assembly 322, the first and second strut inserts 336, 338 are within a thickness of the tubular sleeve 301. First and second openings 324, 328 are arranged for receiving first and second struts 326, 330 into the tubular sleeve 301.

The tubular sleeve 301 may have a third region including first and second portions 306, 308 corresponding to the first and second struts 326, 330. The first and second portions 306, 308 may have elasticity less than the first region 302, and may resemble similar structures in foregoing embodiments. As with the foregoing embodiments, the first and second portions 306, 308 are discretely separate from one another. A popliteal region 340 is preferably between the first and second portions 306, 308 and has elasticity greater than the first and second portions 306, 308.

The orthopedic device 300 has a cable system 312 including at least one cable 314 slidably movable relative to the tubular sleeve 301, as in foregoing embodiments. The cable system 312 has at least one guide 316 connected to the tubular sleeve 301 and is arranged for receiving the at least one cable 314 such that the at least one cable 314 slides within the at least one guide 316 and is routed over the tubular sleeve 301. The at least one guide 316 includes a plurality of guide segments 320 spaced apart from one another and exposing the at least one cable 314 therebetween.

A guide cover 318 covers an entirety of a segment of the at least one guide 316. The cover 318 may be constructed as an adjustment device or anchor for the at least one cable 314, and be adjustable in location over a surface of the tubular support 301. The cover 318 may have a fastener, such as hook and loop, engageable with a corresponding fastener on the tubular support 301.

As shown in FIGS. 6A and 6B, the cable system 312 is arranged circumferentially about the tubular support 301, and takes the place of a strap found in a conventional brace. The cable system 312 may cooperate with a circumferential band 342 to retain the knee support 300 on a leg of user, with the cable system 312 providing additional support to the circumferential band 342. The cable system 312 may extend over the hinge assembly 322 to maintain the circumferential support without impeding use of the hinge assembly 322. Alternatively, the cable system 312 may be routed underneath the hinge assembly 322 to exert circumferential tension over the leg of the user.

Figures 7A, 7B:
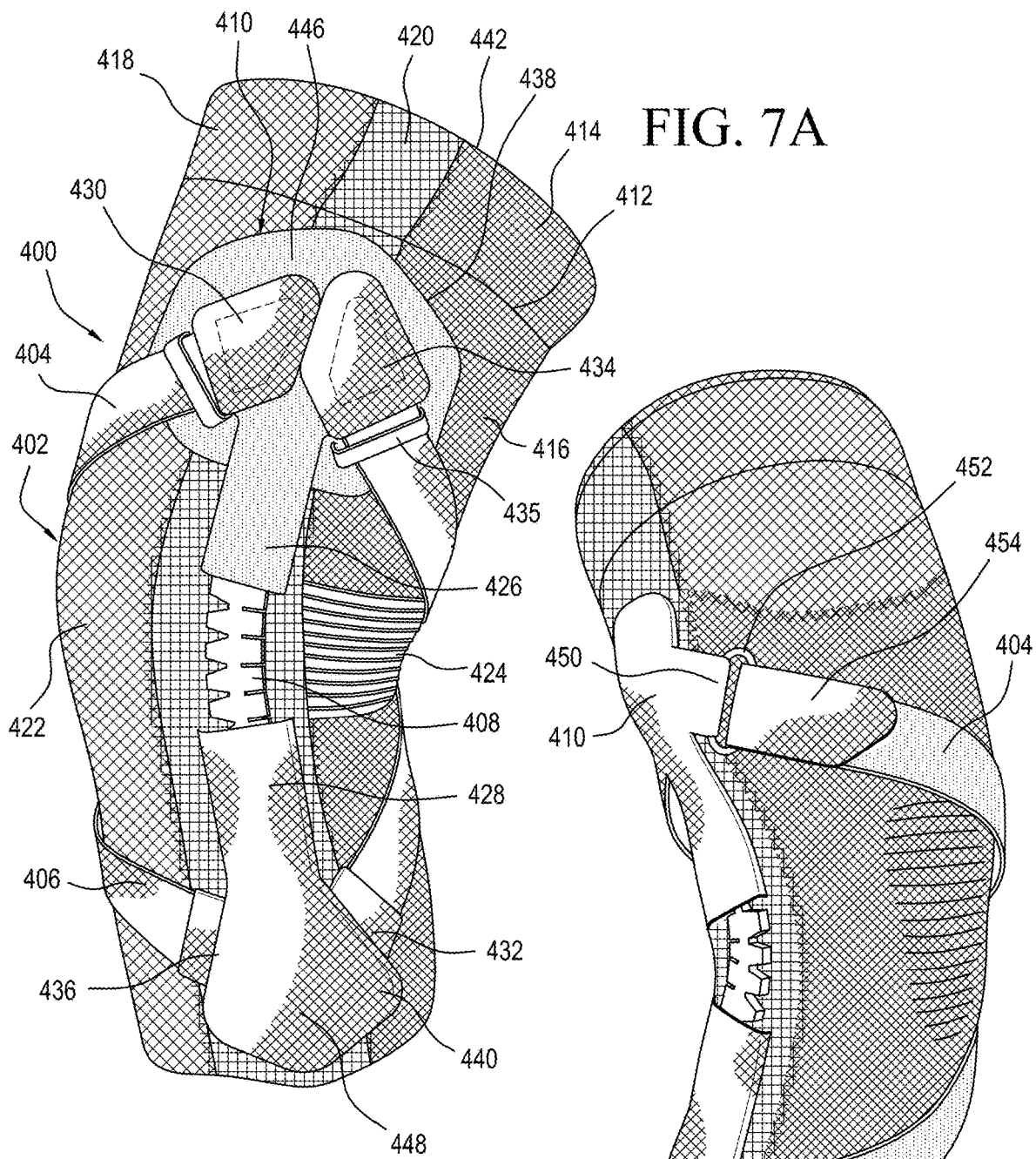
FIG. 7A is a perspective view of another embodiment of a knee support according to an embodiment of an orthopedic device.
FIG. 7B is a perspective view of a variation of the knee support of FIG. 7A.

FIGS. 7A and 7B illustrate another embodiment of an orthopedic device in this embodiment in the form of a functionally knit knee support 400 aimed for treating osteoarthritis of the knee. While the orthopedic device in this embodiment is a functionally knit orthopedic device, the teachings of the disclosure are equally applicable to other types of flexible orthopedic devices and to orthopedic devices in general. The knee support defines a main body panel arranged in this embodiment as a tubular sleeve 402, and has first and second straps 404, 406 arranged to spiral about an outer surface of the tubular sleeve 402, and intersect at a predetermined location. The operation and purpose of the straps 404, 406 for treatment of osteoarthritis of a knee are described in U.S. Pat. No. 7,198,610, granted Apr. 3, 2007, and incorporated herein by reference. The location of the intersection of first and second straps 404, 406 advantageously overcomes the problems of existing straps which intersect over a hinge directly on a medial or lateral side of the brace, which location is not effective for treating osteoarthritis.

The knee support 400 includes a hinge support 410 located along at least one side of the knee support 400, and extends into upper and lower regions of the knee support relative to a central or knee portion. The hinge support 410 is arranged to support or position a hinge 408, and provides anchor areas 446, 448 for the first and second strap 404, 406. The hinge support 410 defines sleeves 426, 428 for receiving portions of the hinge 408 to secure the hinge 408 relative to the tubular sleeve 402, and enable removal of the hinge 408. For example, a different type of hinge, such as a hinge having different stiffness or articulation (four-bar, polycentric, biasing bar), may easily replace an existing hinge.

The hinge support 410 may serve as anchor points for the first and second straps 404, 406. According to the illustrated embodiment, the hinge support 410 is located along either the medial or lateral sides of the knee support 400, and generally along the anterior-posterior plane. Indeed, the hinge support 410 extends between upper and lower regions of the tubular sleeve 402 along one of the medial and lateral sides of the knee support 400. The hinge support 410 may be articulated at the anterior and posterior knee portions 422, 424 of the tubular sleeve 402 to accommodate a natural contour of a leg.

The hinge support 410 may be preferably more rigid than the tubular sleeve 402, although it may be pliant to permit easy contouring of the knee support 400 to the leg of the user. Nonetheless, the hinge support 410 preferably provides greater stability for securing elements, such as straps and a hinge, than the knitted tubular support 402.

In an example, the hinge support 410 is formed from a material having greater rigidity than the knitted structure of the tubular sleeve 402. By way of example, lower or second ends 432, 436 of the first and second straps 404, 406, are permanently or removably secured to a lower or second portion 448 the hinge support 410. By "permanently" secured, it is intended to mean that it is not readily removable by a user, and from normal usage of the knee support 400, a user cannot remove the lower end from the tubular sleeve 402 without significant difficulty. By "removably" secured, it is intended to mean during normal use a user can detach the lower end 432, 436 from the hinge support 410.

In the configuration of being permanently secured, the lower ends 432, 436 may be pivotally secured to the hinge support 410, and extend upwardly in a spiraling manner to an upper or first portion 446 on the hinge support 410. Upper or first ends 430, 434 of the first and second straps 404, 406 are removably secured to the upper or first portion 446 of the hinge support 410. Preferably, the upper or first portion 446 of the hinge support 410 comprises hook receivable material and the upper or first ends 430, 434 having corresponding hook material engageable with the upper or first portion 446. To guide the first and second strap 404, 406, a guide 435, such as a loop, is proximate or at the upper or first portion 446. The upper or first portion 446 is sufficiently sized to accommodate both upper or first ends 430, 434 without overlap.

The upper and lower portions 446, 448 may include first and second stays 438, 440 to provide reinforcement to the straps 404, 406, and possible tension they may exert on the tubular sleeve 402. The stays 438, 440 may be semi-rigid to provide additional support beyond the hinge support 410 and material of the tubular sleeve 402. The stays 438, 440 may be permanently secured or removably secured to or within the hinge support 410. The hinge 408 may overlap the stays 438, 440 whereby the stays 438, 440 may cover a greater portion of the tubular sleeve 402 than hinge arms of the hinge 408, and may serve to distribute pressure exerted by the hinge arms.

The tubular sleeve 402 defines different regions of elasticity, wherein the tubular sleeve 402 includes a main panel 416 that generally possesses a baseline elasticity to comfortably and functionally support a leg. The tubular sleeve 402 includes an upper cuff 414 that may function and be structurally arranged similarly to aforementioned embodiments. The upper cuff 414 preferably has a lower band 412 that is located above the hinge support 410 so the hinge support 410 and stays 438, 440 it may contain do not interfere with folding the upper cuff 414 between the engaged and disengaged configurations, with a proximal edge 442 extending over the hinge support 410.

The tubular sleeve 402 may include a first region of elasticity 418, as in preceding embodiments, on the anterior side of the knee support 400, and may be more rigid or having a contour to embrace or add further support to the knee over the main panel 416. The tubular sleeve 402 may also include a second region of elasticity 420 along or in line with the hinge support 410. The second region of elasticity 420 may be more rigid than the main panel 418, and operates with the hinge support 410 to provide greater rigidity along a direction in which the hinge 408 extends.

Referring to the embodiment of FIG. 7B, a variation of the knee support 400 of FIG. 7A includes angled extensions 450 extending from the hinge support 410 to accommodate the spiraling and angling of the first and second straps 404, 406. A D-ring or other suitable attachment 452 extends from the extensions 450 and permits the first and second straps 404, 406 to secure over itself at first ends 454 to set the length of the straps 404, 406. Although not depicted, the second ends of the straps 404, 406 may be similarly modified to secure onto themselves.

Figure 7C:
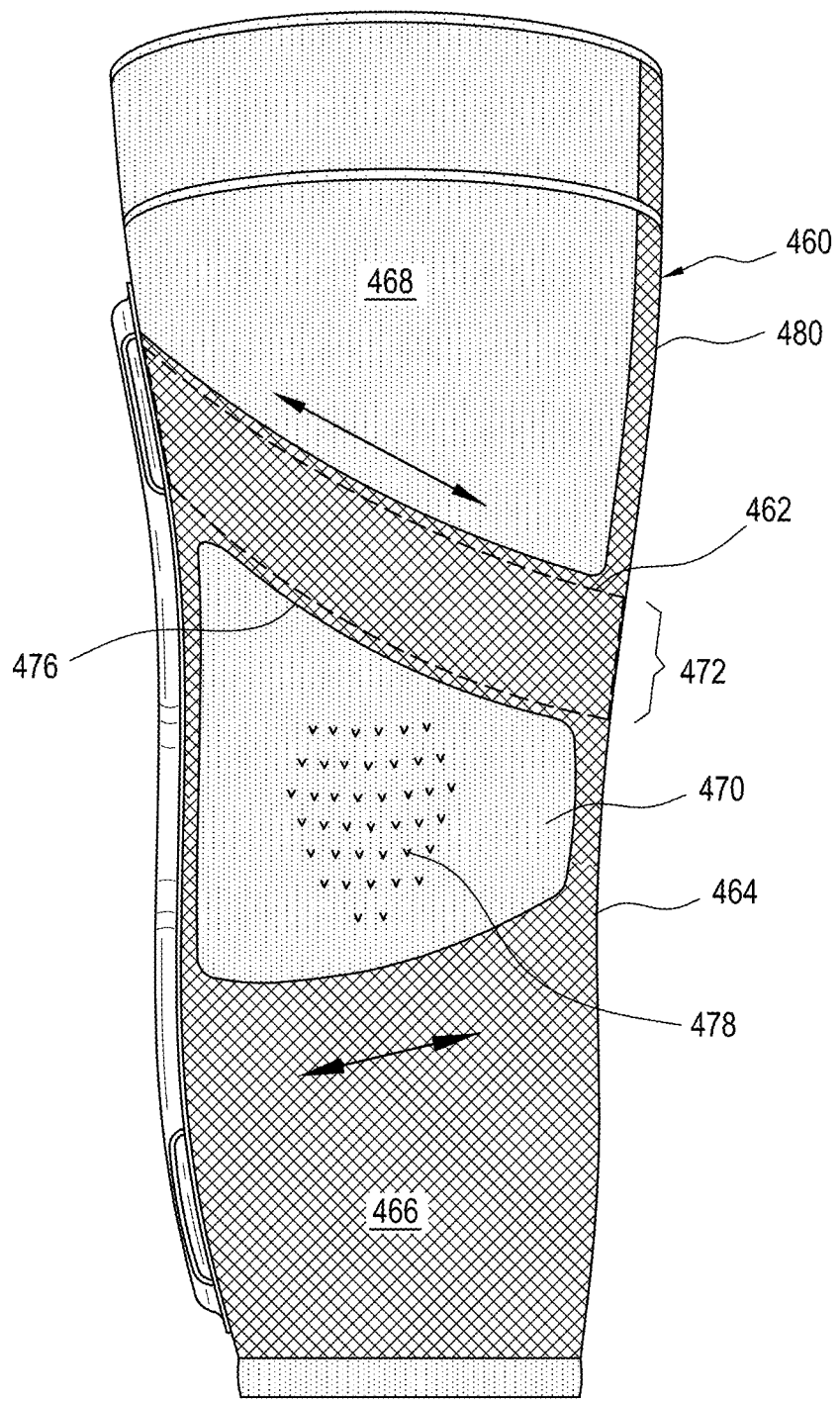
FIG. 7C is a schematic view of a variation of the knee support of FIG. 7A.

FIG. 7C exemplifies a variation of the knee support 460 of FIG. 7A including zones formed by the textile support that are arranged in combination with straps 462, 464. The knee support has a first zone 466 that has greater compressibility and less elasticity than an adjacent, second zone 468. The first zone 466 preferably is arranged to extend at least about the tibia of the user and further extends above the knee, by having a sub-zone 472. The first zone 466 generally surrounds a knee region 470, formed from the same material of the second zone 468, that has substantially greater flexibility than the first zone 466, and further includes a patella or third zone 478, which may have even greater flexibility than the second zone 468 so as not to inhibit flexure of the knee.

With the combination of the first, second and third zones 466, 468, and 478, and their relative flexibility and compressibility (i.e., padding) imparted by the knitted structure of the knee support 460 itself, the knitted structure may mitigate a need for a separate patella buttress or reduce the size of a patella buttress. Indeed, the periphery 476 of the first zone 466 about the second zone 468 in the knee area may be circular or at least continuously surrounding the knee, and thereby provide compression about the patella of the knee. The third zone 478 is comparably the most flexible of the first, second and third zones 466, 468, and 478.

The first zone 466 may be arranged, as shown in FIG. 7C, so that the straps 462, 464 extend over the first zone 466 as opposed to the second zone 468, thereby providing more comfort to the user by being able to better distribute forces exerted onto the user from tensioning of the straps 462, 464 than the second zone 468. For example, the first zone 466 includes the subzone 472 having a width proximate to a width of the first strap 462. The second zone 468 may extend above the knee and first zone 466, so as to provide greater flexibility to the thigh of the user which may undergo more volume changes than the lower leg, as in the tibia region, due in part to the conical shape of the leg. The first zone 466 may extend along a lateral or medial side of the knee support 460 to provide some degree of rigidity compared to the second zone 468 for better stabilization, and/or may be provided in combination with a hinge thereby providing a less elastic region of the knee support 460. Alternatively or in supplement, the lateral and medial sides of the knee support 460 may include a fourth zone 480 having greater stiffness than other zones to complement or provide lateral stability, whether or not an additional hinge is provided with the knee support 460.

The knitted structure and corresponding zones may have different surface textures according to usage of the user. For example, the first zone may have a more sliding resistant texture to inhibit the straps from sliding outside of the first zone while tensioned about the user. Another example may be an inner pocket arranged to receive a buttress or pad, as in the buttress 520 of FIG. 8B. The inner pocket may receive the buttress and have a surface texture that is comfortable to the user but inhibits slippage against the user's skin. The different zones may be distinguished from one another by color, knitted pattern, shape, contrast and other means for demarcating different zones.

The inner pocket may be overlaid on or formed by the main panel, and may be elastic or inelastic. For example, the inner pocket may be constructed from an inelastic material that is stitched to the main panel which may be elastic or an elasticized fabric. In this manner, the support at a region, such as corresponding to a patella of a user, may be elastic on the outer side of the support so as to cause compression against the knee with a buttress or pad, with the pocket or the sheet forming a layer of the pocket located on an inner side of the support and resisting stretching adjacent to the user's knee. The elasticized fabric tensions over the knee and the buttress, whereas the inner side with the inelastic pocket or sheet forming a part thereof, resists the elasticity. A similar construction may be formed proximate and along hinges or stays.

Figure 7D:
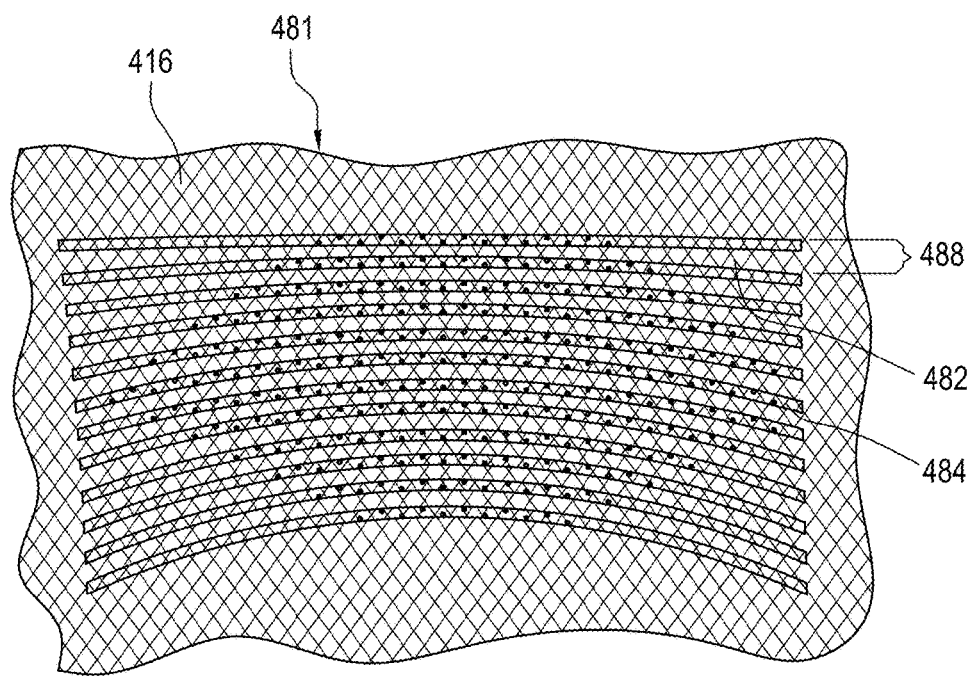
FIG. 7D is a schematic view of a popliteal region in the knee support of FIG. 7A in a non-tensioned configuration.
Figure 7E:
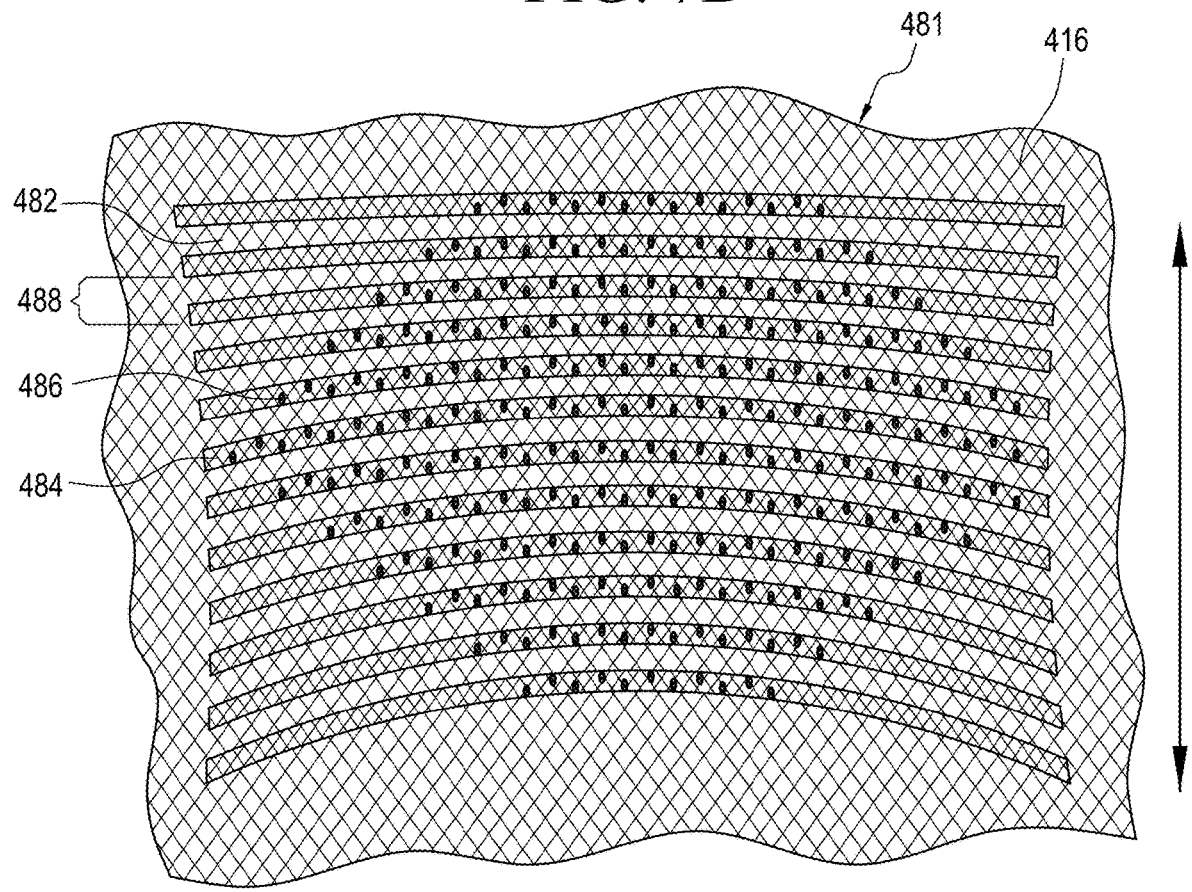
FIG. 7E is a schematic view of the popliteal region of FIG. 7D in a tensioned configuration.

FIGS. 7D and 7E exemplify how the orthopedic device in any of the disclosed embodiments and variations thereof may be arranged with variable ventilation according to tensioning, flexure or configurations the knee support may undergo during use. For example, in a popliteal region 481 or posterior of the knee, the main panel 416 may have a first flexibility and when the popliteal region 481 is tensioned or stretched, the popliteal reveals openings 486 locally formed within the popliteal region 481.

The popliteal region 481 has zones or bands 482 through which the openings 486 preferably do not extend, and an underlying zone 484 from the bands 482 and between such band 482 whereat the openings 486 are formed. While the openings 486 are formed in a predetermined manner, they are contracted and minimally open in a resting, non-tensioned configuration. As the popliteal region 481 is stretched, the openings 486 expand to provide ventilation and additional stretchability within the popliteal region 481. The bands 482 may be constructed from segments of knitted textile that possess the same structure as areas of the main panel 416 adjacent to the popliteal region 481, and a distance 488 between the bands increases as the main panel is tensioned. The underlying zone 484 may have a smaller thickness than the bands 482, so as to increase flexibility within the popliteal region 481.

Figure 8A:
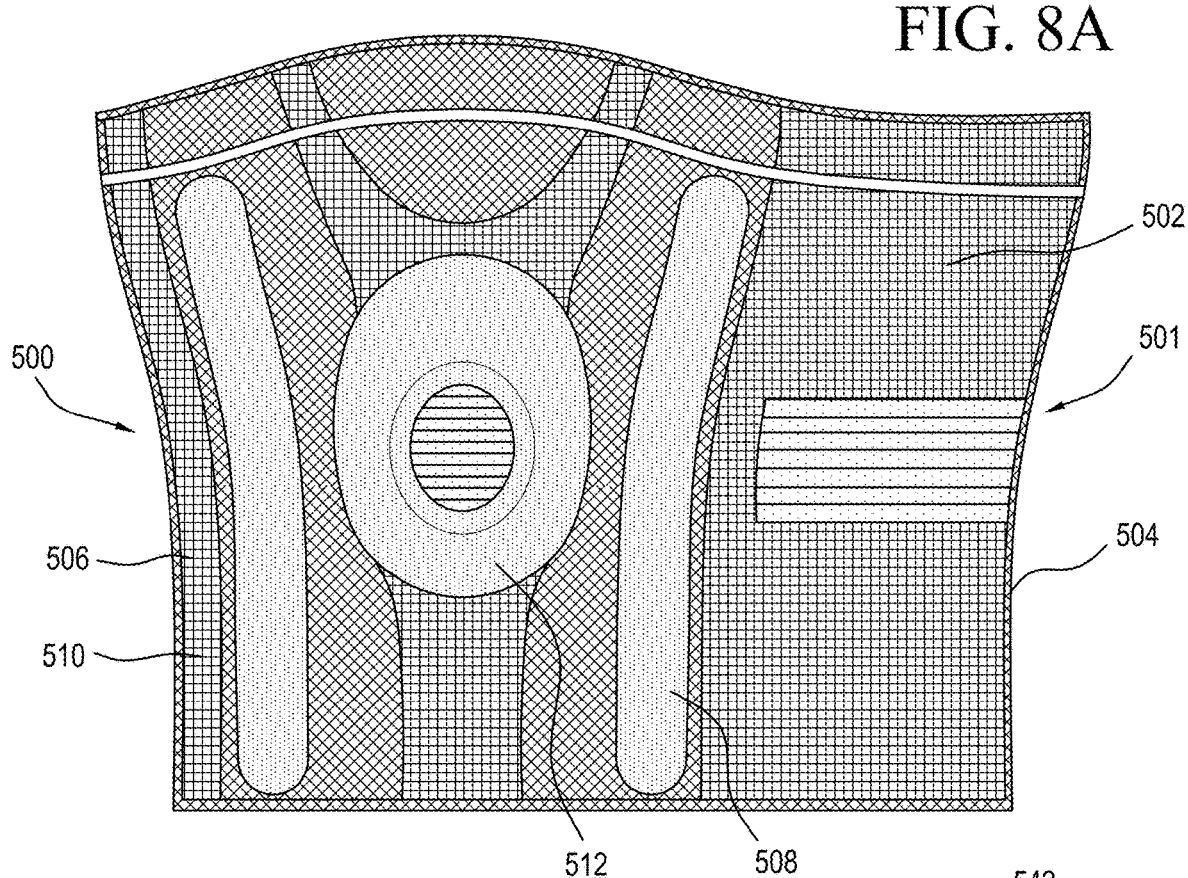
FIG. 8A is a plan view of a knee support according to an embodiment of an orthopedic device in an open configuration.

FIG. 8A depicts an exemplary embodiment of an interior surface 501 of a main panel 501 of a knee support 500. In this embodiment, the main panel 501 may be securable along longitudinal side portions 504, 506 to form a tubular structure. The interior surface 502 may support various stays, bolsters and pads, including stays 508, 510, and a patella pad 512. These stays, bolsters and pads may be removably secured or permanently secured to the main panel 501.

Figure 8B:
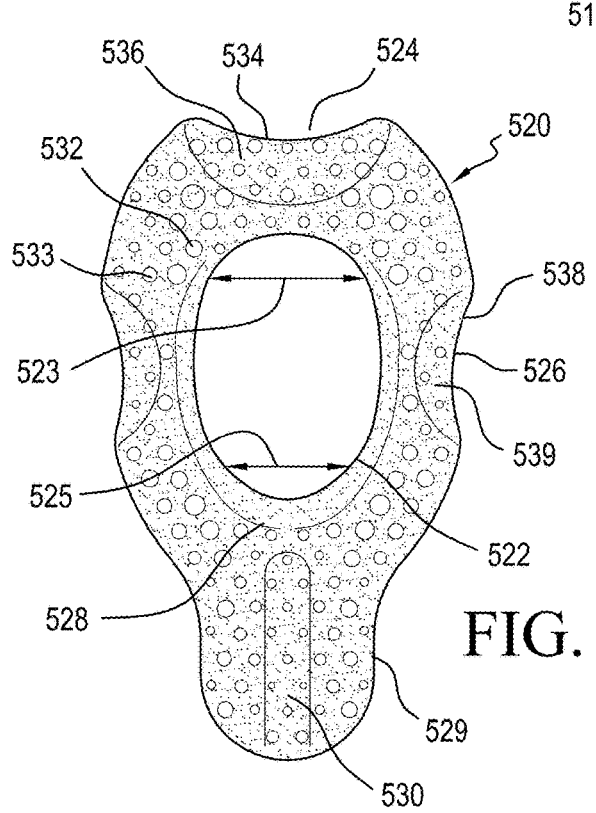
FIG. 8B is a plan view of a patella buttress for use in the aforementioned embodiments of knee supports according to an embodiment of an orthopedic device.

FIG. 8B depicts an exemplary patella pad 520 that may be removably or permanently secured to a knee support 500. The patella pad 520, as depicted showing an outer surface with the inner surface being generally planar in a flat configuration and adapted to be secured to the tubular sleeve of a knee support 500, has peripheral relief portions 524, 526 that are provided for reducing pressure and improving flexure according to flexion and extension of a knee.

The top relief portion 524 has an arcuate cut-out 534 along the periphery and a corresponding concave relief 536. This configuration provides pressure relief on top of the patella and negates pressure on the knee from above the patella. The lateral relief portions 526 likewise have an arcuate cut-out 538 and a corresponding concave relief 539, which provides for better flexure of the patella pad 520, and anatomically contours to the side of the knee during flexion of the knee.

The patella pad 520 defines an opening 522, that may preferably have an oval and non-uniform shape with a greater width at an upper portion 523 and a narrower width at a lower portion 525, to better receive and anatomically contour to the shape of a patella. Below the lower portion 525, there is a segment formed as a patella tendon support zone 528 that leads to a lower extension 529 having an elongate recess 530 or concave relief on the patella ligament. The elongate recess 530 is recessed relative to the patella tendon support zone 528, which is formed in part by a generally circumferential width of the patella pad 520 about the opening 522. This structure advantageously allows the patella pad 520 to provide adequate support to a user's tibial tuberosity but mitigates undesired pressure points by means of the elongate recess 530.

The generally circumferential width gradually tapers to the opening 522 or an inner periphery of the patella pad 520, and yet further tapers to the outer periphery of the patella pad 520, along which the relief portions 524, 526, 536 are located. The relief portions 524, 526, 536 are noted as having a concave configuration relative to the inner surface, and the portions outside of the concave configuration are generally convex relative to the inner surface. The relief portions 524, 526, 536, by virtue of their concave configuration, provide desired flexibility to the patella pad 520 and mitigate pressure points between the patella pad 520 and a user's leg.

The patella pad 520 may define a grip pattern 532 that may be uniform or variable relative to the location of individual grip elements 533. For example, the grip elements 533 may have a small size about the inner periphery of the patella pad 520 and the within the concave reliefs, relative to areas outside of these areas where the grip patterns may be bigger along the convex portions of the patella pad 520. The grip pattern and elements 532, 533 advantageously prevent undesired translation of the patella pad 520 along the skin of a user.

Figure 8C:
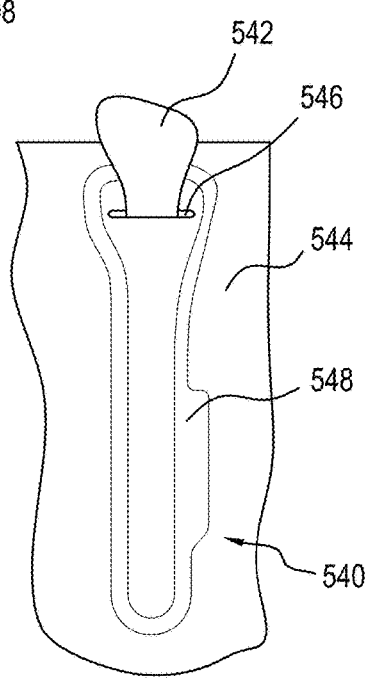
FIG. 8C is an elevational view of a stay for use in the aforementioned embodiments of knee supports according to an orthopedic device.

FIG. 8C exemplifies how a removable stay system 540 may be provided within the knitted structure of a panel 544 for an orthopedic device 500. Specifically, the panel 544 may form a pocket 548 that can accommodate a removable stay 542 through a slit 546 providing access to the pocket 548. The pocket 548 preferably has a profile that closely approximates the stay 542 so the stay remains securely and snugly maintained within the pocket 548.

Figure 9:
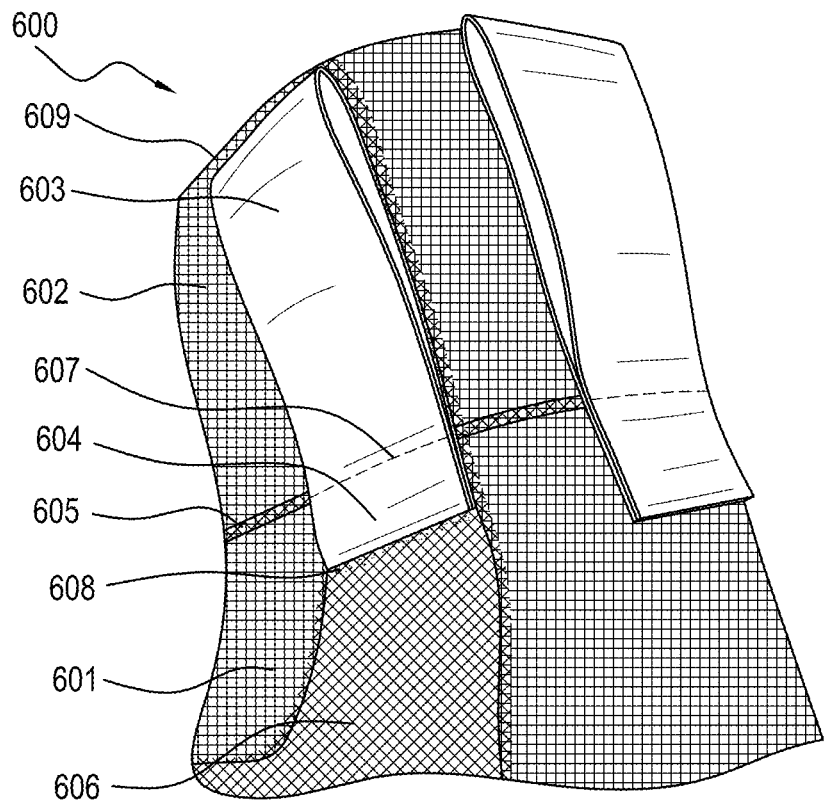
FIG. 9 is a partial sectional view of pull tabs according to an embodiment of an orthopedic device.

Turning now to FIG. 9, a schematic detail view of an embodiment of an orthopedic device is shown, such as in an ankle brace 600. In this particular detail view, an upper portion of the ankle brace 600 is shown comprising a main body panel arranged in this embodiment as a tubular body 601, with an upper cuff 602 divided from the tubular body 601 by an upper folding portion 605. An uppermost periphery of ankle brace 600 is defined by first edge 609. Handles arranged in this embodiment as pull tabs 603 are attached to the ankle brace 600 at an attachment portion 604, which may attach at a stay 606 similar to the foregoing embodiments and demarcated in this embodiment by a different fabric color and texture than surrounding portions of tubular body 601. Pull tabs 603 may attach to the tubular body 601 by reinforcement stitching 607 and/or by adhesive 608.

By attaching the pull tabs 603 at a location below the folding portion 605, the pull tabs 603 are advantageously protected from wear and tear relating to operating the folding portion 605, and are better ensured to be fully visible and exposed so as to be gripped when the upper cuff 602 is in the disengaged configuration. Additionally, this location helps to arrange the pull tabs 603 such that they are fully concealed below the first edge 609 when the upper cuff 602 is in the engaged configuration. A frictional element 610 is proximate the pull tabs 603 and may underlie the frictional element 610, as depicted.

Thus pull tabs 603 are, when the ankle brace 600 is in the engaged configuration of FIG. 9, completely concealed by the upper cuff 602; when the ankle brace 600 is in the disengaged configuration, the pull tabs 603 are configured to be fully erect so as to be easy for a user to find and grasp.

The stay 606 may be a separate element, or may be formed simply by the knitted zone in which it is located, as compared to other knitted zones of the tubular body. For example the stay 606 is knitted from an inelastic material having greater thickness and/or compressibility than neighboring knitted zones.

Figure 10:
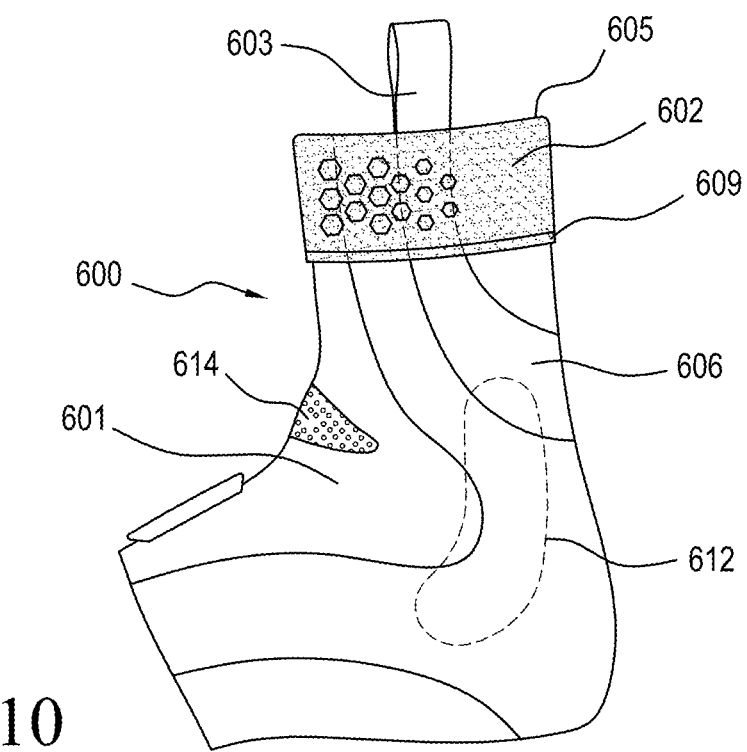
FIG. 10 is an elevational view of an ankle support according an embodiment of an orthopedic device.
Figure 11A:
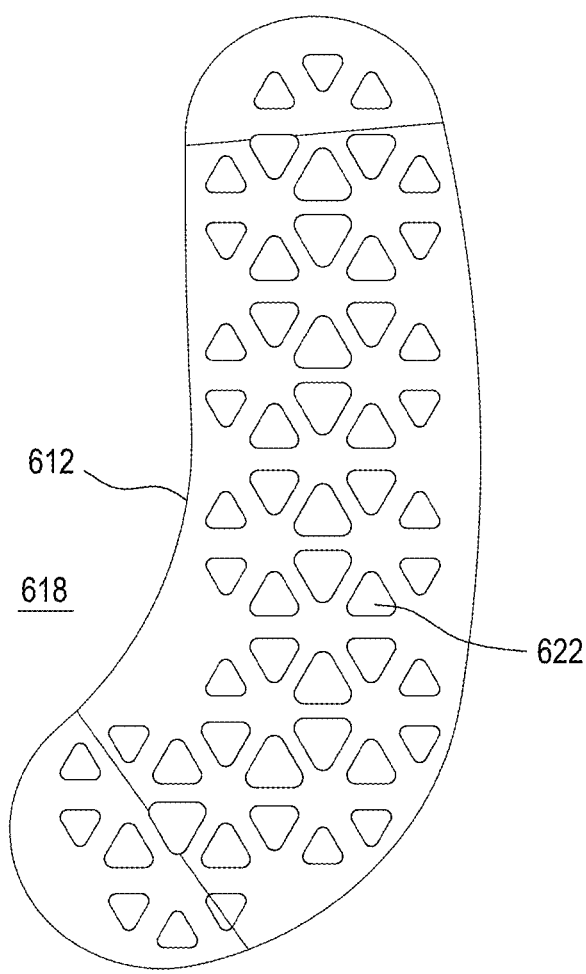
FIG. 11A is a plan view of a buttress or pad useable in the embodiment of FIG. 10.
Figure 11B:
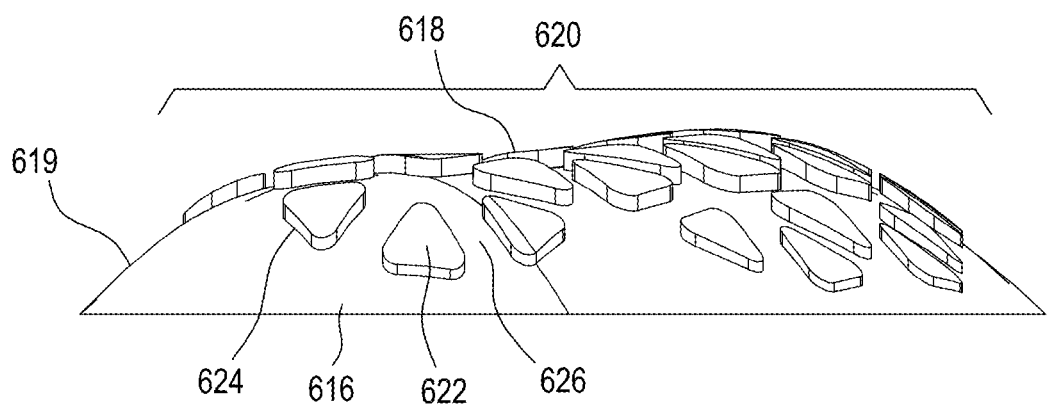
FIG. 11B is an elevational view of the buttress or pad of FIG. 11A.

FIG. 10 depicts an elevational view of the ankle support 600 of FIG. 9 in a disengaged configuration, depicting in particular how stay 606 may be arranged to extend through tubular body 601 in a particular configuration in order to advantageously apply pressure along critical portions of a limb, in this embodiment a region proximate to the Achilles tendon of a user. This structure has the added advantage of providing an improved path for the handles arranged in this embodiment as pull tabs 603 to exert forces on the ankle brace 600, thus avoiding damage to the ankle brace 600 during donning and doffing.

The ankle support 600 may include a substantially open knit zone 614 at a dorsal joint of the ankle and foot. The open knit zone 614 offers significant breathability. The ankle support 600 may include an ankle buttress or malleolus pad 612 arranged for being secured along an interior surface of the tubular body 610. A malleolus pad may be located on both medial and lateral sides of the tubular body 601.

The ankle buttress 612 may be formed as any of the aforementioned buttresses. In this instance, the ankle buttress 612, on an inner side 618 directed toward the user, defines a curved profile 619 leading from a flat side 616 on the outer side of the buttress 612. The inner side 618 defines a surface relief 620 having a plurality of grip elements 622 protruding from the profile of the buttress 612. The grip elements 622 have a height 624 extending above the profile, with a plurality of channels 626 extending between the grip elements 622 to facilitate breathability and permit a broader surface area of the buttress 612 over the affected region of the ankle. The outer side of the buttress 612 is flat and adapted to have its surface flush with the tubular body 601.

Figure 12A:
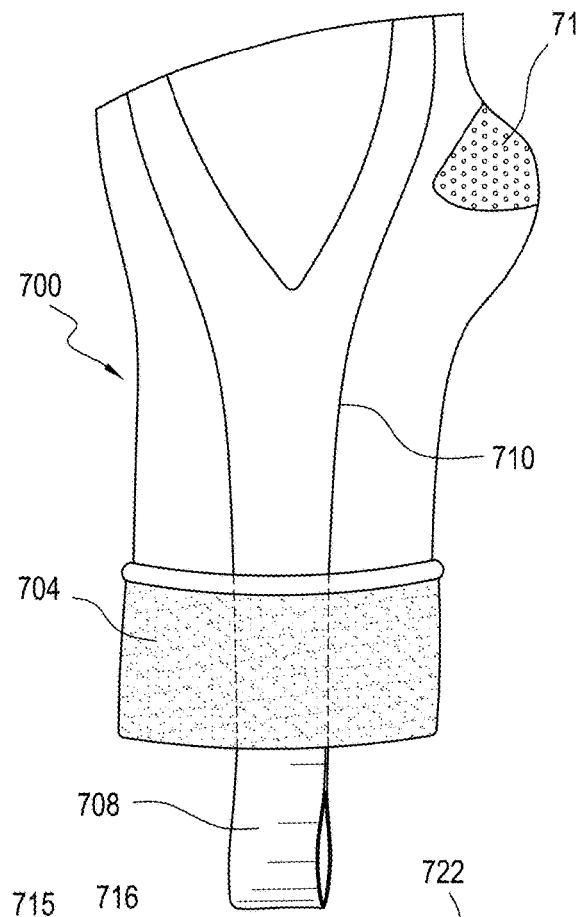
FIGS. 12A and 12B are opposite schematic views of first and second sides of a wrist support according to an embodiment of an orthopedic device.
Figure 12B:
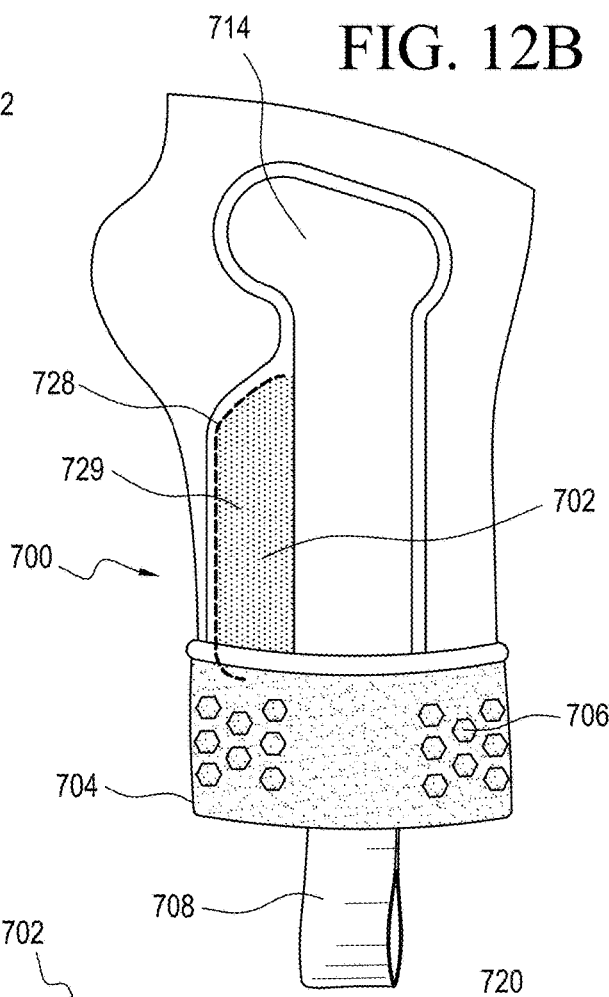
Figure 12C:
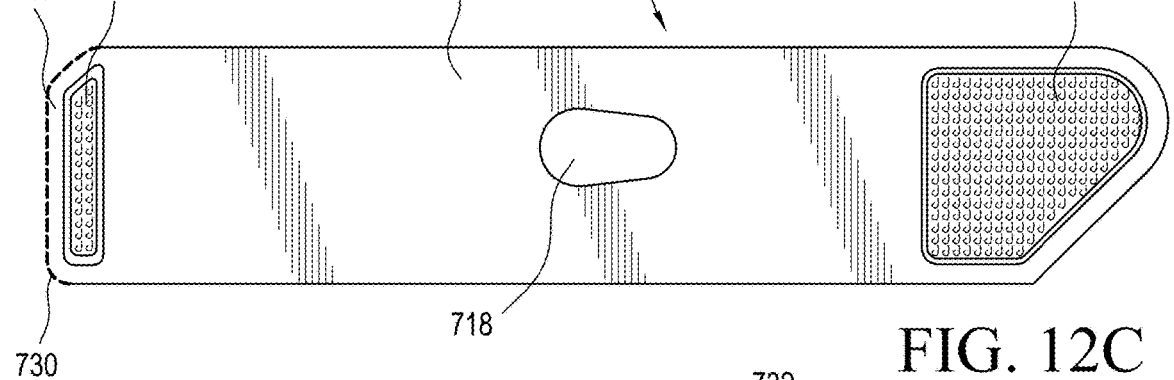
FIG. 12C is a strap useable in the wrist support of FIGS. 12A and 12B.
Figure 12D:
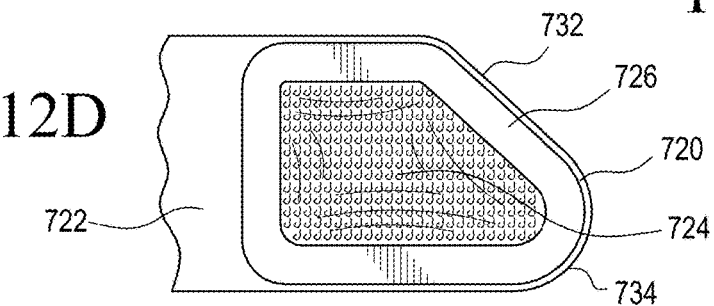
FIG. 12D is a detail view of a strap end of the strap in FIG. 12C.

FIGS. 12A and 12B represent an orthopedic device in the form of a wrist support 700. A strap 702 is arranged to secure to the wrist support 700, and has cooperating elements to assure the strap 702 is properly placed about the wrist support 700. For example, the wrist support 700 defines markings or a knitted pattern 728 proximate in shape to an end of the strap having a similar profile 730. In this manner, the strap 702 is assured of being properly placed about the wrist support 700, particularly since the strap 702 defines an opening 718 which is configured and dimensioned extend about a user's wrist, with the opening 718 about the ulnar nerve of the user to minimize discomfort by the user.

The wrist support 700 includes a cuff 704 as in preceding embodiments of the orthopedic device along with frictional elements 706. A pull tab 708 is provided which is in line with a less elastic or inelastic zone 710 of the wrist support 700. The zone 710 allows for the wrist support to maintain its integrity while it is donned by the user, as compared to neighboring zones of the wrist support, which may be knitted, as in preceding embodiments. Alternatively, the zone 710 may comprise a stay 714 reinforcing the wrist support, as in FIG. 12B, or there may be at least two pull tabs, with each corresponding to a side of the wrist support, and have a corresponding zone or stay associated therewith. An open knit area 712 may be provided between the joint between an index finger and thumb, and may possess characteristics as in preceding embodiments.

The strap 702 may be formed from a knitted material or other suitable material or combination of materials. The strap 702 may be inelastic or elastic. The strap 702 may define first and second surfaces, whereby one surface 722 is preferably formed from non-hook engageable material, whereas the other surface (not shown) has hook-receivable material located along a length or entirety of length thereof.

A first end 715 of the strap 702 may define a hook region 716 arranged to secure to corresponding hook-receivable material 729 on the wrist support 700, particularly where the wrist support and strap defined corresponding profiles 728, 730 to guide the user on where to mount the first end of the strap 702.

The strap 702 has a second end 720 adapted to secure to the second surface of the strap 702. The second end 720 forms a hook region 724 preferably having a raised profile relative to the first surface 722 of the strap 702. The hook region 724 is welded onto the first surface 722 of the strap 702, and a border 726 surrounds the hook region 724, wherein the border 726 does not bear hooks but may be a reinforced area surrounding the hook region, providing greater rigidity than the material forming the strap 702. The improved rigidity of the border 726 makes it easier for the entirety of the second end 720 to disengage from the second surface of the strap 702 when pulled by a user.

As with the first end 715 having a profile 730, the second end 720 also defines a distinct profile 732 different from the profile 730. The profile 732 is arranged with a sloping point 734 that converges to make it is easy for a user to grasp the second end 720 for applying and removing the second end 720 from the second surface of the strap 702. When combined with the border 726, the point 734 contributes to better donning and doffing of the strap 702 from the wrist support 702, thereby enabling consistent wear and ease of use of the wrist support. The hook region 716 may be arranged similarly with a border as the second end 720.

Figures 13A, 13B:
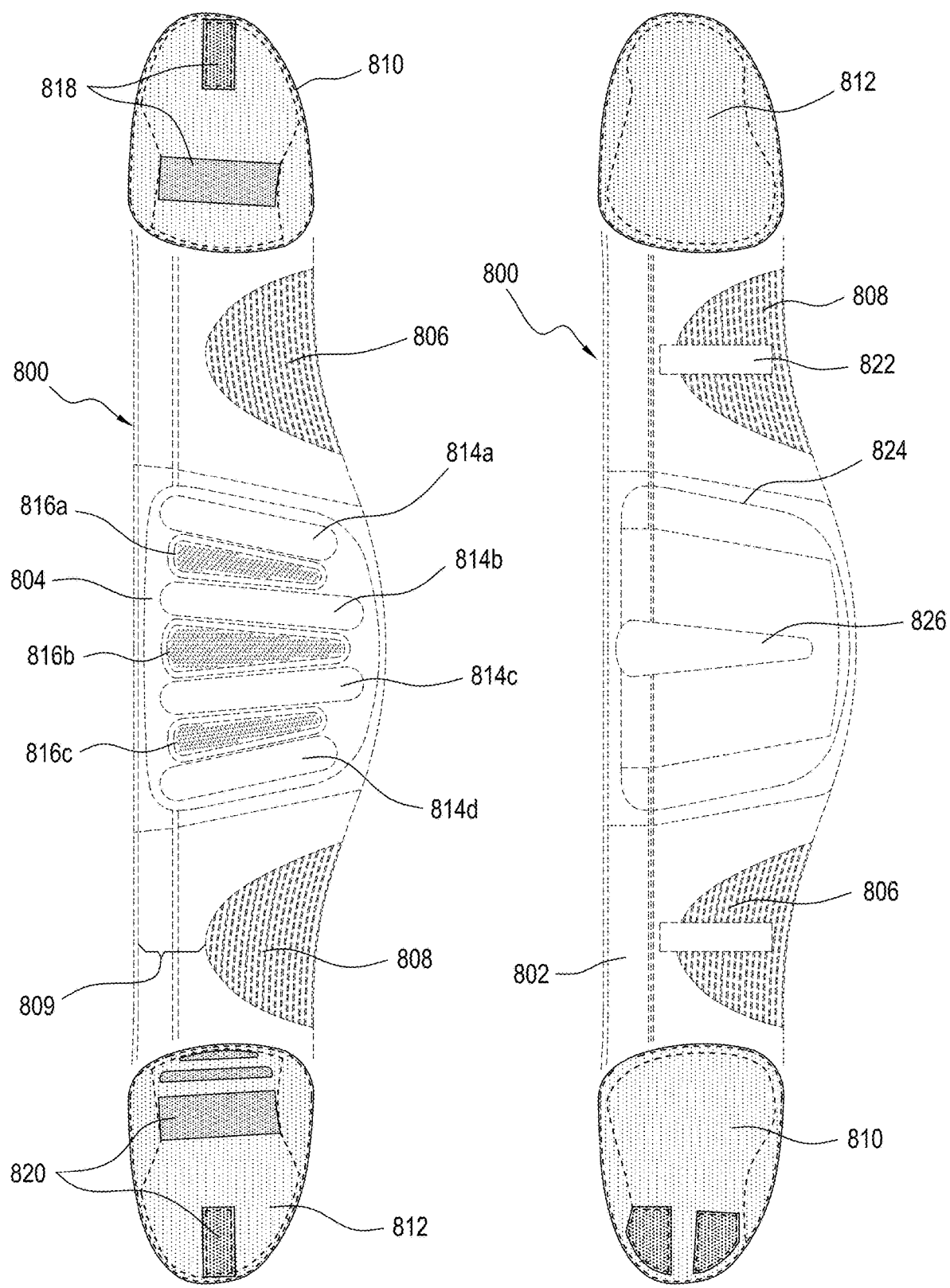
FIGS. 13A and 13B show first and second sides of a lumbar support according to an embodiment of an orthopedic device.

FIGS. 13A and 13B exemplify the orthopedic device in the form of a lumbar support 800. The lumbar support 800 defines a main panel 802 having a first elasticity, and a posterior panel 804 preferably formed from an inelastic material or a material having less elasticity than the main panel 802. The posterior panel 804 may be secured to the main panel 802, such as in overlapping the main panel 802, or may be knitted with the main panel 802. The lumbar support 800 has first and second closure ends 810, 812, having corresponding fastener elements 818, 820 for engaging the first and second closure ends 810, 812. The elasticity of the main panel 802 may be inhibited in a corresponding posterior region 824 along an opposed side of the main panel 802 than the side on which the posterior panel 804 is located. A hook receivable region 826 may be located within the posterior region 824 for receiving a lumbar pad (not shown). The hook receivable region 826 may be applied to the main panel 802, and is preferably inelastic so as not to cause the lumbar pad to detach therefrom.

The lumbar support 800 defines lateral regions 806, 808, located about the lateral or outer sides of the hip of a user. The lateral regions 806, 808 have an elasticity different from the main panel 802, for example the lateral regions 806, 808 may have greater elasticity than the main panel 802, and are shaped with a profile that corresponds to the hip joint, as in an arcuate form. In the depicted embodiment, the lateral regions 806, 808 extend short of a height of the lumbar support 800, such that the less elastic main panel 802 rises to an upper edge of the lumbar support 800 a height 809. This height 809 enables the lumbar support 800 to still consistently tension about a user's waist, with the lateral regions 806, 808 extending below to locally accommodate the hip of the user. The lateral regions 806, 808 may include elongate stays 822 to stabilize or accommodate the increased elasticity in the lateral regions 806, 808.

The posterior panel 804 may be provided in combination with a plurality of rigid or substantially rigid stays 814a-814d that may be removably attached to the posterior panel 804, or enclosed by the posterior panel 804. The stays 814a-814d may be formed by plastics or malleable materials such as aluminum to be customized to the lordosis of the user. The stays 814a-814d are separated by clearances that may be formed by perforated regions 816a-816c of the posterior panel 804. While the perforated regions 816a-816c remains inelastic, they offer greater breathability than regions of the posterior panel 804, and the main panel 802 to compensate for the stays 814a-814d.

In any of the aforementioned embodiments and variations thereof, an orthopedic device may include straps for added function to the device. The straps can be external, or they may be knitted as cables or laces into the brace, as discussed above, or they can be knitted as zones of low elasticity into the brace. For external straps, markers may be provided on the strap to guide the user how to apply the strap or adjust the cables for tensioning or reducing tension in the strap. The markers can be knitted into the knitting of the orthopedic device or otherwise applied, such as by heat transfer.

In another embodiment, straps or bands can be laminated into or over the orthopedic device. The orthopedic device may be knitted in a manner including zones of hook receivable material or structure, and the corresponding strap may include hook material for engaging the hook receivable zone. Loops may be formed directly by the orthopedic device for guiding the strap or cables.

It is possible to knit the orthopedic device in such a way that the active components are only visible on the inside, while the outside of the brace is more uniform in appearance. This enables the user to see how the brace functions before donning, while not being "too flashy" when worn.

While the disclosure discusses embodiments for the knee and ankle, orthopedic device embodiments of the disclosure may be used with other limbs, joints and anatomical portions including the torso, shoulder, elbow, wrist/hand, hip, knee, and foot/ankle.

Not necessarily all such objects or advantages may be achieved under any embodiment of the invention. Those skilled in the art will recognize that the invention may be embodied or carried out to achieve or optimize one advantage or group of advantages as taught without achieving other objects or advantages as taught or suggested.

The skilled artisan will recognize the interchangeability of various components from different embodiments described. Besides the variations described, other known equivalents for each feature can be mixed and matched by one of ordinary skill in this art to construct an orthopedic brace under principles of the present invention. Therefore, the embodiments described may be adapted to orthopedic systems for securing, supporting or comforting limbs or other anatomy.

Although this invention has been disclosed in certain preferred embodiments and examples, it therefore will be understood by those skilled in the art that the present invention extends beyond the disclosed embodiments to other alternative embodiments and/or uses of the invention and obvious modifications and equivalents. It is intended that the scope of the present invention disclosed should not be limited by the disclosed embodiments described above, but should be determined only by a fair reading of the claims that follow.

The invention claimed is:

1. An orthopedic device having first and second open ends, the orthopedic device arranged into an engaged configuration for use of the orthopedic device and a disengaged configuration for donning and doffing the orthopedic device, the orthopedic device comprising:
    a main body defining inner and outer surfaces, and forming a tubular sleeve, the main body having first and second ends; and
    a first cuff continuously extending from the first end of the main body and having a tubular shape, the first cuff defining inner and outer surfaces and having a first periphery defining the first open end of the orthopedic device in the engaged configuration;
    wherein the first cuff has a textile structure distinct from that of the main body, such that the textile structure of the first cuff includes silicone yarns disposed on at least the inner surface of the first cuff;
    wherein the silicone yarns are exposed only in a dot profile only on the inner surface of the first cuff by being stitched with another yarn covering at least part of the silicone yarns;
    wherein the dot profile comprises a plurality of columns of the exposed silicone yarns configured in an alternating arrangement;
    wherein the dot profile of the textile structure is formed by intarsia knitting;
    wherein the textile structure is formed by knitting the silicone yarn with the another yarn selected from the group consisting of: kevlar, fusible nylon monofilament, dynema, and spandex.

2. The orthopedic device of claim 1, further comprising a first band defined along a peripheral edge of the first cuff and defining a periphery of the first open end when the orthopedic device is in an engaged configuration.

3. The orthopedic device of claim 2, further comprising a second band connecting the first cuff to the main body, the second band defining a location of the first cuff and facilitating folding of the first cuff over the main body at the second band.

4. The orthopedic device of claim 3, wherein the first cuff is arranged to fold over the outer surface of the main body from the second band, and circumferentially extends on the main body in the disengaged configuration to expose the inner surface of the first cuff, the second band forming the periphery of the first open end in the disengaged configuration.

5. The orthopedic device of claim 3, wherein the second band has a different knitted structure than the first cuff.

6. The orthopedic device of claim 2, wherein the first band has greater elasticity than the first cuff.

7. The orthopedic device of claim 1, further comprising a handle secured to the inner surface of the main body and extending past the first end of the main body and to the first cuff.

8. The orthopedic device of claim 1, wherein the silicone yarns are pretensioned in the textile structure.

9. The orthopedic device of claim 1, wherein the dot profile is formed by a plurality of raised surfaces.

10. An orthopedic device having first and second open ends, the orthopedic device arranged into an engaged configuration for use of the orthopedic device and a disengaged configuration for donning and doffing the orthopedic device, the orthopedic device comprising:
    a main body defining inner and outer surfaces, and forming a tubular sleeve;
    a first cuff extending from the main body and having a tubular shape, the first cuff defining inner and outer surfaces and having a first periphery defining the first open end in the engaged configuration;
    wherein the first cuff has a textile structure distinct from that of the main body, a first segment of the textile structure includes silicone yarns on the inner surface of the first cuff, the textile structure having a pattern of exposed silicone yarns only on the inner surface of the first cuff and on at least part of a circumference of the first cuff;
    wherein the first cuff is arranged to fold over the outer surface of the main body in the disengaged configuration, such that the outer surface and first periphery of the first cuff are adjacently against the outer surface of the main body, the main body defining a second periphery defining the first open end in the disengaged configuration;
    wherein the silicone yarns are exposed only in a dot profile only on the inner surface of the first cuff by being stitched with another yarn covering at least part of the silicone yarns; wherein the dot profile comprises a plurality of columns of the exposed silicone yarns configured in an alternating arrangement.

11. An orthopedic device having first and second open ends, the orthopedic device arranged into an engaged configuration for use of the orthopedic device and a disengaged configuration for donning and doffing the orthopedic device, the orthopedic device comprising:
    a main body defining inner and outer surfaces, and forming a tubular sleeve, the main body having first and second ends;

a first cuff continuously extending from the first end of the main body and having a tubular shape, the first cuff defining inner and outer surfaces and having a first periphery defining the first open end of the orthopedic device in the engaged configuration;

wherein the first cuff has a textile structure distinct from that of the main body, a first segment of the textile structure includes silicone yarns on the inner surface of the first cuff, the textile structure having a pattern of exposed silicone yarns only on the inner surface of the first cuff and on at least part of a circumference of the first cuff;

a first band defined along a peripheral edge of the first cuff and defining a periphery of the first open end when the orthopedic device is in an engaged configuration, the first band having greater elasticity than the first cuff; and a second band connecting the first cuff to the main body, the second band defining a location of the first cuff and facilitating folding of the first cuff over the main body at the second band;

wherein the first cuff is arranged to fold over the outer surface of the main body from the second band, and circumferentially extends on the main body in the disengaged configuration to expose the inner surface of the first cuff, the second band forming the periphery of the first open end in the disengaged configuration;

wherein the silicone yarns are exposed only in a predetermined profile only on the inner surface of the first cuff by being stitched with another yarn covering at least part of the silicone yarns; wherein the predetermined profile comprises a plurality of columns of the exposed silicone yarns configured in an alternating arrangement.

* * * * *